United States Patent [19]

Brandt et al.

[11] Patent Number: 4,654,039
[45] Date of Patent: Mar. 31, 1987

[54] HYDROGEL-FORMING POLYMER COMPOSITIONS FOR USE IN ABSORBENT STRUCTURES

[75] Inventors: Kerryn A. Brandt; Stephen A. Goldman; Thomas A. Inglin, all of Cincinnati, Ohio

[73] Assignee: The Proctor & Gamble Company, Cincinnati, Ohio

[21] Appl. No.: 746,152

[22] Filed: Jun. 18, 1985

[51] Int. Cl.$^4$ ............................................. A61F 13/16
[52] U.S. Cl. .................................. 604/368; 521/149; 526/207
[58] Field of Search ............... 604/368, 369, 370, 371, 604/372, 373, 360, 378, 379; 521/149; 526/81, 207, 240, 317

[56] References Cited

U.S. PATENT DOCUMENTS

| | | |
|---|---|---|
| 3,901,236 | 8/1975 | Assarsson et al. |
| 4,062,817 | 12/1977 | Westerman .................. 260/17.45 G |
| 4,076,663 | 2/1978 | Masuda et al. ............. 260/17.4 GC |
| 4,286,082 | 8/1981 | Tsubakimoto et al. ............. 526/240 |
| 4,340,706 | 7/1982 | Obayashi et al. ..................... 526/207 |
| 4,473,689 | 9/1984 | Login et al. ........................... 526/81 |
| 4,535,098 | 8/1985 | Evani et al. .......................... 521/149 |

FOREIGN PATENT DOCUMENTS 75510 4/1983 European Pat. Off.
3313344 10/1984 Fed. Rep. of Germany.

OTHER PUBLICATIONS

Arakawa Chemical Industries, Ltd.; "ARASORB A Super Absorbent Polymer"; undated.
Stockhausen Inc.; "FAVOR SAB-901"; Jul. 1983.
BASF AG; "LUQUASORB HC 9780-Superabsorbent Based on Polyacrylic Acid for Aqueous Fluids"; undated.
Sanyo Chemical Industries; "Super Absorbent Polymer-SANWET IM-300/SANWET IM-1000" Oct. 1982.

Primary Examiner—John D. Yasko
Attorney, Agent, or Firm—George W. Allen; Jack D. Schaeffer; Steven J. Goldstein

[57] ABSTRACT

The present invention relates to improved hydrogel-forming polymer compositions which can be used as absorbents in absorbent structures and absorbent articles such as diapers, sanitary napkins and the like. Such hydrogel-forming polymer compositions are substantially water-insoluble, slightly cross-linked, partially neutralized polymers which are prepared from unsaturated polymerizable, acid group-containing monomers and cross-linking agents. These hydrogel-forming polymer materials, upon imbibing fluids, form hydrogels. Such polymer materials have relatively high gel volume and relatively high gel strength as measured by shear modulus of the hydrogel which forms therefrom. Such polymer materials also contain relatively low levels of extractable polymer material which can be extracted therefrom by contact with synthetic urine. Preferred hydrogel-forming polymers having these characteristics can be prepared by polymerizing the acid group-containing monomers in their free acid form at relatively low monomer concentrations, preferably using relatively low polymerization temperatures. Absorbent structures and absorbent articles containing these dried hydrogel-forming polymer materials are also disclosed.

37 Claims, 1 Drawing Figure

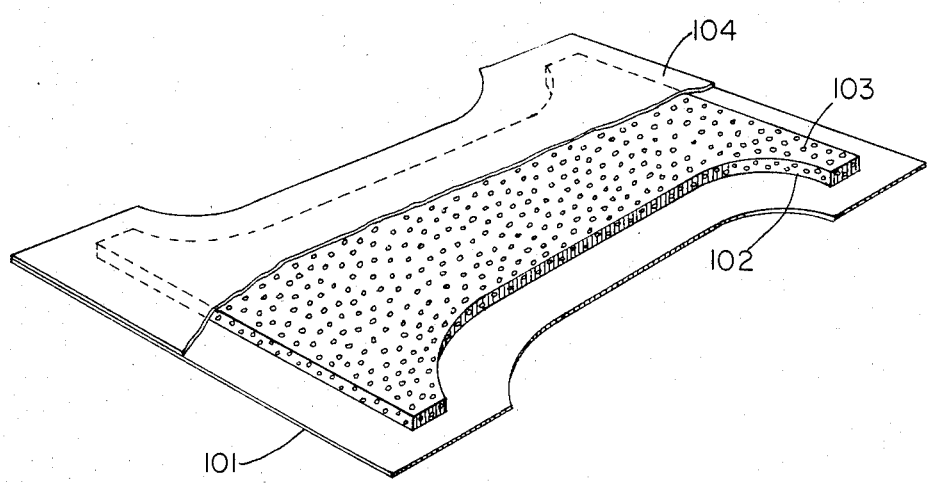

HYDROGEL-FORMING POLYMER COMPOSITIONS FOR USE IN ABSORBENT STRUCTURES

FIELD OF THE INVENTION

This invention relates to improved hydrogel-forming polymer compositions and to a process for their preparation. Such hydrogel-forming polymers are those which, upon contacting fluids (i.e. liquids) such as water or body fluids, imbibe such fluids and thereby form hydrogels. These hydrogel-forming polymer materials are useful as absorbents in absorbent structures which can be incorporated into absorbent articles such as disposable diapers, adult incontinence pads, sanitary napkins and the like.

BACKGROUND OF THE INVENTION

Water-insoluble hydrogel-forming polymers are materials which are capable of absorbing large quantities of fluids such as water and body waste and which are further capable of retaining such absorbed fluids under moderate pressures. These absorption characteristics of such materials make them especially useful for incorporation into absorbent articles such as disposable diapers. Harper et al; U.S. Pat. No. 3,669,103; Issued June 13, 1972 and Harmon; U.S. Pat. No. 3,670,731; Issued June 20, 1972, for example, both disclose the use of hydrogel, i.e., "hydrocolloid," materials in absorbent products.

Frequently hydrogel-forming aborbent materials comprise polymers of polymerizable unsaturated carboxylic acids or derivatives thereof, such as acrylic acid and/or alkali metal and alkyl acrylates. These polymers are rendered water-insoluble by cross-linking the carboxyl group-containing polymer chains using conventional cross-linking agents such as di- or poly-functional monomer materials. The degree of cross-linking in hydrogel and hydrogel-forming materials not only determines their water-solubility but is also an important factor in establishing two other characteristics of fluid absorbing hydrogels, i.e., absorbent capacity and gel strength. Absorbent capacity of "gel volume" is a measure of the amount of water or body fluid which a given amount of hydrogel-forming material will absorb. Gel strength relates to the tendency of the hydrogel formed from such material to deform or "flow" under an applied stress.

Hydrogel-forming materials useful as absorbents in absorbent structures and articles such as disposable diapers must have adequately high gel volume and the hydrogels formed therefrom must have adequately high gel strength. Gel volume must, of course, be sufficiently high to enable the hydrogel-forming material to absorb a significant amount of the fluid which such material encounters in the absorbent article. Gel strength must be such that the hydrogel formed does not deform and fill to an unacceptable degree the capillary void space in the absorbent structure or article, thereby inhibiting both absorbent capacity of the structure or article and fluid distribution throughout the structure or article.

One known type of hydrogel-forming material having the requisite gel volume and gel strength characteristics for use in absorbent articles is the water-absorbing starch resin disclosed in Masuda et al; U.S. Pat. No. 4,076,663; Issued Feb. 28, 1978. Such materials are prepared by graft polymerizing unsaturated monomers onto polysaccharides (such as starch or cellulose) and by cross-linking the resulting graft copolymer. While such materials are quite suitable for use as absorbents in absorbent articles, such materials must utilize starch or cellulose as an essential raw material for their preparation. It is preferred that these starch (or cellulose) materials be pretreated by heating in order to swell or gelatinize them. Given the enormous volume of raw materials which would be required for use in successfully marketed absorbent articles such as disposable diapers, it would be desirable to identify additional types of efficient hydrogel-forming absorbents which, unlike the starch resins, do not consume significant amounts of energy in their preparation and which do not depend on agricultural raw materials of potentially uncertain availability for their preparation.

Hydrogel-forming materials which essentially comprise only cross-linked polymerized unsaturated monomers, and no starch or cellulose moieties, are also known. Such materials are described, for example, in Tsubakimoto et al; U.S. Pat. No. 4,286,082; Issued Aug. 25, 1981; in Westerman; U.S. Pat. No. 4,062,817; Issued Dec. 13, 1977 and in Obayashi et al; U.S. Pat. No. 4,340,706; Issued July 20, 1982. These materials are typified by cross-linked polyacrylates which are prepared by copolymerizing acrylic acid and acrylate monomers in relatively high concentration at polymerization temperatures generally above 20° C.

While these known starch-free hydrogel-forming materials can be synthesized with sufficient gel volume and gel strength characteristics to be utilized in absorbent articles, there is an additional characteristic of such materials which is unrecognized in the foregoing patents and which, in the prior art materials, tends to diminish the effectiveness of such hydrogel-forming materials as absorbents in absorbent articles. This additional characteristic concerns the level of extractable polymer material in the hydrogel-forming material. Even though the hereinbefore referenced U.S. Pat. No. 4,286,082 describes hydrogels which are said to have low "water-solubles" for safety reasons, it has been discovered that the starch-free hydrogel-forming polymers of this '082 patent, as well as other known starch-free hydrogel-forming polymers, nevertheless contain significant levels of extractable polymer material. This extractable polymer material can be leached out of the formed hydrogel structure by body fluids such as urine during the time period over which such body fluid contacts hydrogel-forming material in an absorbent article. Without being bound by theory, it is believed that such polymer material extracted by body fluid in this manner can alter both the chemical and physical characteristics of the body fluid to the extent that the fluid is more slowly absorbed and more poorly held by the hydrogel-containing absorbent article. Such a situation, of course, then contributes to undesirable leakage of body fluid from the article. On the other hand, synthesis of hydrogel-forming material in a manner which maximizes gel volume (while maintaining adequate gel strength) but which minimizes the extractable polymer content thereof, will result in improved hydrogel-forming materials which are especially useful in those absorbent articles which can be worn for relatively extended periods of time without leakage.

In view of the foregoing, it is an object of the present invention to provide improved hydrogel-forming polymer compositions which are free of starch or other polysaccharide-based polymer material but which nevertheless have desirably high gel volume and gel strength characteristics and which have acceptably low levels of extractable polymer therein.

It is a further object of the present invention to provide a process for preparing such improved hydrogel-forming polymer compositions.

It is a further object of the present invention to provide absorbent structures and articles such as disposable diapers which utilize such improved hydrogel-forming polymer materials as absorbents for body fluids.

SUMMARY OF THE INVENTION

In its composition aspects, the present invention relates to a substantially water-insoluble, slightly cross-linked, partially neutralized, hydrogel-forming, polymer material which is useful as an absorbent of body fluids. Such a hydrogel-forming polymer consists essentially of from about 50 mole percent to 99.999 mole percent of polymerized unsaturated polymerizable acid group-containing monomers and from about 0.001 mole percent to 5 mole percent of a cross-linking agent. Such a hydrogel-forming polymer composition has a degree of neutralization of at least about 25% and is furthermore substantially free of graft polymerized polymer moieties such as starch or cellulose. Such a hydrogel-forming polymer composition, upon neutralization to a degree of neutralization of at least about 50%, furthermore has or would have a gel volume of at least about 20 grams of synthetic urine per gram of hydrogel-forming material, gel strength characteristics such that the hydrogel formed from such a composition exhibits a shear modulus of at least about 2000 dynes/cm$^2$, an initial extractable polymer content, i.e., after one hour in synthetic urine, of no more than about 7.5% by weight of hydrogel-forming polymer and an equilibrium extractable polymer content, i.e., at equilibrium in synthetic urine of no more than about 17% by weight of hydrogel-forming polymer. Preferred classes of polymer materials of this type are those having particular relationships (a) between gel volume and equilibrium extractable polymer content, and (b) between gel volume and shear modulus of the hydrogel formed.

In its process aspects, the present invention relates to a process for preparing certain of these substantially water-insoluble, slightly cross-linked, partially neutralized, hydrogel and/or hydrogel-forming polymer materials. Such a process comprises the steps of preparing a reaction mixture consisting essentially of particular amounts of unsaturated polymerizable acid group-containing monomers, cross-linking agent and optionally free radical initiator in an aqueous medium; subjecting this reaction mixture to polymerization conditions to produce a substantially water-insoluble, slightly cross-linked polymer material having under certain conditions particular gel volume, gel strength and extractable polymer content characteristics; and neutralizing at least a portion of the acid functional groups of the resulting polymer material with salt-forming cations to form a partially neutralized polymer material having a degree of neutralization of at least about 25%.

The reaction mixture prepared in aqueous medium consists essentially of from about 5% to 35% by weight of acid group-containing monomers in the free acid form, from about 0.001 mole percent to 5 mole percent of the cross-linking agent based on total monomers used and from 0% to about 5 mole percent of the free radical initiator based on total monomers used. The reaction mixture must furthermore be substantially free of graft polymerizable polymer moieties such as starch or cellulose.

Polymerization conditions to which this reaction mixture is subjected are those which are sufficient to produce a polymer material which has or would have, upon subsequent neutralization to a degree of neutralization of at least about 50% and upon subsequent drying, a gel volume of at least about 20 grams of synthetic urine per gram of hydrogel-forming polymer, a gel strength such that the hydrogel formed therefrom exhibits a shear modulus of at least about 2000 dynes/cm$^2$, an initial extractable polymer content, i.e., after one hour in synthetic urine, of no more than 7.5% by weight of hydrogel-forming material and an equilibrium extractable polymer content, i.e., at equilibrium in synthetic urine, of no more than about 17% by weight of hydrogel-forming material. Such polymer materials furthermore have a relationship between gel volume, v, and equilibrium extractable polymer content, e, which is defined by the equation: $e \leq 0.23v - 3.0$. The hydrogel material formed in this process may optionally be dried in order to prepare absorbent hydrogel-forming polymer materials which re-form hydrogels upon subsequent contact with water or body fluids.

In its article-of-manufacture aspects, the present invention relates to an absorbent structure suitable for use in disposable absorbent articles. Such an absorbent structure comprises from about 50% to 98% by weight of such a structure of hydrophilic fiber material and from about 2% to 50% by weight of the structure of discrete particles of substantially water-insoluble, slightly cross-linked, partially neutralized, substantially dry hydrogel-forming polymer material. This hydrogel-forming polymer material has a degree of neutralization of at least about 25% and is furthermore substantially free of graft polymerized polymer moieties such as starch or cellulose. Such a hydrogel-forming polymer material, upon neutralization to a degree of neutralization of at least about 50%, has or would have a gel volume of at least about 20 grams of synthetic urine per gram of hydrogel-forming polymer, gel strength characteristics such that the hydrogel formed therefrom exhibits a shear modulus of at least about 2000 dynes/cm$^2$, an initial extractable polymer content, i.e., after one hour in synthetic urine, of no more than about 7.5% by weight of hydrogel-forming polymer, and an equilibrium extractable polymer content, i.e., at equilibrium in synthetic urine, of no more than about 17% by weight of hydrogel-forming polymer. Preferred classes of polymer materials for use in such articles are those having particular relationships (a) between gel volume and equilibrium extractable polymer content, and (b) between gel volume and shear modulus of the resulting hydrogel. The present invention also provides absorbent articles such as disposable diapers which utilize such polymer-containing absorbent structures.

BRIEF DESCRIPTION OF THE DRAWING

The drawing submitted herewith represents a cutaway view of a disposable diaper which is a preferred configuration for the absorbent articles herein.

DETAILED DESCRIPTION OF THE INVENTION

The substantially water-insoluble, slightly cross-linked, partially neutralized, hydrogel-forming polymer materials of this invention are those which are prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof.

Olefinically unsaturated carboxylic acid and carboxylic acid anhydride monomers include the acrylic acids typified by acrylic acid itself, methacrylic acid, ethacrylic acid, alpha-chloroacrylic acid, alpha-cyano acrylic acid, beta-methyl-acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-styryl acrylic acid (1-carboxy-4-phenyl butadiene-1,3), itaconic acid, citraconic acid, mesaconic acid, glutaconic acid, aconitic acid, maleic acid, fumaric acid, tricarboxy ethylene and maleic acid anhydride.

Olefinically unsaturated sulfonic acid monomers include aliphatic or aromatic vinyl sulfonic acids such as vinylsulfonic acid, allyl sulfonic acid, vinyltoluenesulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

Of all the foregoing unsaturated, acid-containing monomers, preferred monomers include acrylic acid, methacrylic acid, and 2-acrylamido-2-methyl propane sulfonic acid. Acrylic acid itself is especially preferred.

The hydrogel-forming polymer materials of the present invention must be prepared primarily from the acid group-containing monomers as hereinbefore described. Generally, from about 50 mole percent to 99.999 mole percent, and more preferably from about 75 mole percent to 99.99 mole percent of the hydrogel-forming polymer material will be prepared from such acid group-containing monomers. Two or more different monomer types of the hereinbefore described acid group-containing monomers may be copolymerized in order to provide hydrogel-forming polymer material of this requisite acid group-containing monomer content.

While at least 50 mole percent of the hydrogel-forming polymer compositions herein must be prepared from acid group-containing monomers, some non-acid monomers may also be used to prepare the hydrogel-forming polymer compositions herein (prior to neutralization). Such non-acid monomers can include, for example, the water-soluble or water-dispersible esters of the foregoing acid-containing monomers as well as monomers which contain no carboxyl or sulfonic acid groups at all. Optional non-acid monomers can thus include, for example, carboxylic acid or sulfonic acid ester-containing monomers, hydroxyl group-containing monomers, amide group-containing monomers, amino group-containing monomers, nitrile group-containing monomers and quaternary ammonium salt group-containing monomers. These non-acid monomers are well known materials and are described in greater detail, for example, in Masuda et al.; U.S. Pat. No. 4,076,663; Issued Feb. 28, 1978, and in Westerman; U.S. Pat. No. 4,062,817; Issued Dec. 13, 1977, both of which are incorporated herein by reference. If present at all, such non-acid monomers will be used only to such an extent that, prior to neutralization, no more than about 50% mole percent of the polymer compositions herein are prepared from such non-acid monomers.

It should be noted that the foregoing optional non-acid monomers include only those monomers which will copolymerize with the essential acid-containing monomers used to prepare the hydrogel-forming polymers herein. The hydrogel-forming polymer compositions of this invention must not, however, contain any significant amount of other moieties, e.g., polymer moieties, onto which the acid group-containing monomers will graft polymerize. Polymer moieties such as polysaccharides, e.g., starch or cellulose, are an essential element of several known types of hydrogel-forming materials which have especially desirable and useful absorbent properties. It has now been discovered that hydrogel-forming polymer compositions of equal or better fluid absorbing performance characteristics vis-a-vis such prior art materials can be provided in the form of polymer compositions which are substantially free of graft polymerizable polymer moieties such as starch. Thus, it has furthermore been discovered that an element heretofore thought to be essential to the realization of exceptionally desirable hydrogel absorption performance can be eliminated while nevertheless providing hydrogel-forming polymer materials which are especially useful in absorbent articles.

A second essential element of the hydrogel-forming polymer compositions herein is a cross-linking agent which serves to render the hydrogel-forming polymer compositions of this invention substantially water-insoluble and which in part serves to determine the gel volume, gel strength and extractable polymer content characteristics of the hydrogels formed from the polymer compositions herein. Suitable cross-linking agents include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages.

Cross-linking agents having at least two polymerizable double bonds include (i) di- or polyvinyl compounds such as divinylbenzene and divinyltoluene; (ii) di- or poly-esters of unsaturated mono- or poly-carboxylic acids with polyols including, for example, di- or triacrylic acid esters of polyols such as ethylene glycol, trimethylol propane, glycerine, or polyoxyethylene glycols; (iii) bisacrylamides such as N,N-methylenebisacrylamide; (iv) carbamyl esters that can be obtained by reacting polyisocyanates with hydroxyl group-containing monomers; (v) di- or poly-allyl ethers of polyols; (vi) di- or poly-allyl esters of polycarboxylic acids such as diallyl phthalate, diallyl adipate, and the like; (vii) esters of unsaturated mono- or poly-carboxylic acids with mono-allyl esters of polyols such as acrylic acid ester of polyethylene glycol monoallyl ether; and (viii) di- or triallyl amine.

Cross-linking agents having at least one polymerizable double bond and at least one functional group reactive with the acid-containing monomer material include N-methylol acrylamide, glycidyl acrylate, and the like. Suitable cross-linking agents having at least two functional groups reactive with the acid-containing monomer material include glyoxal; polyols such as ethylene glycol; polyamines such as alkylene diamines (e.g., ethylene diamine), polyalkylene polyamines, polyepoxides, di- or polyglycidyl ethers and the like. Suitable polyvalent metal cross-linking agents which can form ionic cross-linkages include oxides, hydroxides and weak acid salts (e.g., carbonate, acetate and the like) of alkaline earth metals (e.g., calcium, magnesium) and zinc, including, for example, calcium oxide and zinc diacetate.

Cross-linking agents of many of the foregoing types are described in greater detail in the hereinbefore-referenced U.S. Pat. No. 4,076,663. Of all of these types of cross-linking agents, the most preferred for use herein are the di- or poly-esters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine.

The cross-linking agent will generally comprise from about 0.001 mole percent to 5 mole percent of the resulting hydrogel-forming polymer material. More preferably, the cross-linking agent will comprise from about 0.01 mole percent to 3 mole percent of the hydrogel-forming polymer compositions herein.

After the foregoing monomers and cross-linking agents are reacted to form cross-linked polymer material containing neutralizable acidic functional groups, at least some of these acid groups must be neutralized to form the partially neutralized hydrogel-forming, polymer compositions herein. For purposes of this invention, such hydrogel-forming polymer compositions are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization."

By reacting the foregoing conventional monomer materials and cross-linking agents under certain reaction conditions, and preferably in a certain manner hereinafter described, it has been discovered that novel hydrogel-forming polymer compositions having especially desirable properties can be realized. More particularly, it has been discovered that improved hydrogel-forming polymer compositions consisting essentially of only the acid-containing monomers and cross-linking agents hereinbefore described can be prepared which have or would have, upon subsequent neutralization to a degree of neutralization of at least about 50%, a particular combination of gel volume, gel strength, and extractable polymer content characteristics. This particular combination of characteristics renders these hydrogel-forming polymers, when neutralized to a particular extent, especially useful as absorbents in absorbent structures and articles.

Gel volume refers to the capacity of a given hydrogel-forming polymer material to absorb fluids with which it comes into contact. Gel volume can vary significantly with the nature of the fluid being absorbed and with the manner in which fluid contacts the hydrogel-forming material. For purposes of this invention, gel volume is defined in terms of the amount of synthetic urine absorbed by any given hydrogel-forming polymer in terms of grams of synthetic urine per gram of hydrogel-forming polymer in a procedure hereinafter defined. Since the specific gravity of the synthetic urine is approximately 1.0, gel volume can also be reported in terms of ml of synthetic urine per gram of hydrogel-forming polymer.

The synthetic urine used to define gel volume herein is a salt solution in distilled water with the surface tension of the solution adjusted to 45 dynes/cm with about 0.0025% of an octylphenoxy polyethoxy ethanol surfactant (Triton X-100, from Rohm and Haas Co.). Such a synthetic urine solution comprises 15 parts of 1% Triton X-100, 60 parts NaCl, 1.8 parts of $CaCl_2.2H_2O$, 3.6 parts of $MgCl_2.6H_2O$ and 6000 parts of distilled water.

Gel volume is determined by forming a suspension of about 0.1–0.2 parts of dried hydrogel-forming polymer to be tested with about 20 parts of this synthetic urine. This suspension is maintained at ambient temperature under gentle stirring for about 1 hour so that swelling equilibrium is attained. Using a procedure described in greater detail hereinafter in the TEST METHODS section, the gel volume of the hydrogel-forming polymer in grams of synthetic urine per gram of hydrogel-forming polymer is then calculated from the weight fraction of the hydrogel-forming polymer in the suspension and the ratio of the liquid volume excluded from the formed hydrogel to the total volume of the suspension.

The hydrogel-forming polymer compositions of the present invention are those which have a gel volume of at least about 20 grams of synthetic urine per gram of hydrogel-forming polymer. More preferably, the novel polymer materials herein have a gel volume of from about 25 to 80 grams of synthetic urine per gram of hydrogel-forming polymer. Hydrogel-forming polymer compositions having this relatively high gel volume characteristic are especially useful in absorbent structures and articles since the hydrogels formed from such polymers can, by definition, hold desirably high amounts of discharged body fluids such as urine.

In addition to this relatively high gel volume, the hydrogels formed from the polymer compositions of the present invention must also possess certain gel strength characteristics. Gel strength refers to the propensity of the formed hydrogel material to deform or spread under stress once the polymer material absorbs fluid. For a given type of hydrogel material backbone and cross-linking agent, gel strength will generally decrease as the gel volume parameter increases. It has been found that it is desirable to utilize in absorbent structures and articles those polymer materials which form hydrogels having as high a gel strength as possible consistent with the realization of hydrogels of acceptably high gel volume.

It has also been found that gel strength, i.e. gel deformation tendency, (in the context of hydrogel-forming materials incorporated into absorbent structures and articles) correlates directly with the shear modulus of the hydrogel material which is formed. Accordingly, polymer materials which form hydrogels having sufficient gel strength to be useful in absorbent structures and articles of this invention can be appropriately characterized by specifying gel strength in terms of the shear modulus of the hydrogel materials which are formed.

Shear modulus can be conventionally measured, for example, by a procedure which involves the use of a stress rheometer to determine the ratio of (a) stress applied to a given hydrogel sample to (b) the resulting strain exhibited by the sample. The hydrogel-forming polymer sample tested in this manner is swollen to its gel volume with synthetic urine. Using a procedure described in greater detail hereinafter in the TEST METHODS section, the stress to strain ratio is determined, and the shear modulus of the resulting hydrogel sample in dynes/cm² is then subsequently calculated from this ratio.

The polymer compositions of the present invention form hydrogels having a gel strength such that these hydrogels exhibit a shear modulus of at least about 2000 dynes/cm². More preferably, the hydrogel materials formed herein have a shear modulus within the range of from about 2500 dynes/cm² to 92000 dynes/cm². Without being bound by any particular theory, it is believed that hydrogel materials having high gel strength as reflected in these shear modulus values will resist deformation upon fluid absorption and will have a reduced tendency to flow. Thus, high gel strength materials may actually serve to maintain separation of the individual fibers of hydrophilic fiber material with which the hydrogel-forming polymers herein are conventionally mixed in absorbent structures. Such fiber separation improves both the wicking and absorbent capacity of such absorbent structures. Low gel strength hydrogels, on the other hand, merely flow into void spaces between fibers upon fluid absorption and can thereby actually replace the absorbent capacity of the absorbent structures and articles into which they are incorporated.

In addition to relatively high gel volume and gel strength characteristics, a third essential feature of hydrogel-forming materials which are especially useful as fluid absorbents in absorbent structures and articles relates to the level of extractable polymer material present in such hydrogel-forming material. As noted hereinbefore, it is believed that polymer material extracted by body fluid once hydrogels are formed can alter both the chemical and physical characteristics of the body fluid to the extent that such fluid is more slowly absorbed and more poorly held by the hydrogel-containing absorbent article.

By altering the chemical character of the body fluid, extracted polymer causes fluid to become more poorly held by the hydrogel. This reduces the ultimate capacity of the hydrogel-forming polymer for the body fluid. When leaching of extractable polymer occurs more slowly than the swelling of the hydrogel-forming polymer, which is often the case, fluid absorbed prior to polymer leaching can be released from the hydrogel during the leaching process.

Extractable polymer material leached from the formed hydrogel can also alter the physical character of body fluid (e.g., by increasing fluid viscosity). This altered fluid is more slowly transported through the hydrogel-containing absorbent article and more slowly absorbed by the hydrogel-forming polymer. Transport of body fluid via processes such as wicking is an important performance feature of many absorbent articles. It provides a mechanism for moving fluid from the area of fluid entry into the article to more remote regions of the article. This enables hydrogel-forming polymer in these more remote regions to contact the body fluid and thus contribute to the overall absorbent capacity of the article. After the hydrogel-forming material in the region of fluid entry is used to full capacity, transport of fluid to more remote regions and absorption of fluid by the hydrogel-forming polymer in these more remote regions must be rapid enough to prevent premature leakage of fluid from the article. To the extent that the leaching of polymer from the hydrogel-forming polymer increases fluid viscosity, thereby resulting in slower transport and absorption of body fluid, undesirable leakage of body fluid from the absorbent article is more likely to occur.

Singly or as a result of a combination of these mechanisms, leaching of polymer into the body fluid to be absorbed can result in less efficient utilization of the hydrogel-forming polymer in the absorbent article and a greater incidence of undesirable leakage of body fluid from the article. Therefore, realization of hydrogel-forming polymer compositions having relatively low levels of extractable polymer material is an important feature of the present invention.

For purposes of the present invention, extractable polymer levels can be determined by contacting a sample of hydrogel-forming polymer material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The synthetic urine utilized is the same type of solution hereinbefore described for the gel volume and gel strength determinations. The particular procedure used to determine extractable polymer content of the hydrogel-forming polymer compositions herein is set forth in greater detail hereinafter in the TEST METHODS section.

It has been discovered that hydrogel-forming polymers which are especially useful in absorbent structures and absorbent articles possess two types of extractable polymer content characteristics. In the first place, the hydrogel-forming polymer compositions herein must have an initial extractable polymer content, i.e., the level of extractable polymer which is removed after one hour in contact with synthetic urine, of no more than about 7.5% by weight of the hydrogel-forming polymer. In the second place, such hydrogel-forming polymer compositions must also have an equilibrium extractable polymer content, i.e., the equilibrium level of extractable polymer removed after, for example, sixteen hours in contact with synthetic urine, of no more than about 17% by weight of hydrogel-forming polymer. More preferably, the hydrogel-forming polymer compositions herein have an initial extractable polymer content of no more than about 5% by weight of hydrogel-forming polymer and an equilibrium extractable polymer content of no more than about 10% by weight of hydrogel-forming polymer. It can be seen from these two types of extractables parameters that not only is the total amount of extractable polymer in the hydrogel-forming polymer important, but the rate at which such extractable polymer material is leached can also be a factor which affects absorption performance of the hydrogel-forming polymer.

It has also been discovered that a "preferred" class of hydrogel-forming polymers are those which exhibit a particular relationship between gel volume and equilibrium extractable polymer content. It is, in fact, this "preferred" class of hydrogel-forming polymers which can be prepared in accordance with the particular novel polymer preparation process hereinafter described. This preferred class of hydrogel-forming polymers will have a gel volume, v, in terms of grams of synthetic urine per gram of hydrogel-forming polymer and an equilibrium extractable polymer content, e, in terms of percent extractables by weight of hydrogel-forming polymer wherein the relationship between v and e is defined by the equation: $e \leq 0.23v - 3.0$. More preferably, gel volume, v, and equilibrium extractable polymer content, e, of this preferred class of hydrogel-forming polymers will be defined by the equation: $e \leq 0.073v - 0.37$.

It has further been discovered that an "especially preferred" class of hydrogel-forming polymer materials are those which, in addition to the above preferred relationship between gel volume and equilibrium extractables, also possess a particular relationship between gel volume and gel strength as measured by shear modulus of the resulting hydrogel. More specifically, hydrogel-forming polymers of this "especially preferred" class are those which have a gel volume, v (grams/gram), and which produce hydrogels having a shear modulus, s (dynes/cm$^2$), wherein the relationship between v and s is defined by the equation:

$$\log s \geq -2.494 \log v + 8.090$$

More preferably, gel volume, v, and shear modulus, s, of hydrogels formed from this "especially preferred" class of polymers will be defined by the equation: $\log s \geq -2.568 \log v + 8.221$.

As noted, the hydrogel-forming polymer compositions hereinbefore described, whether broadly defined or defined as "preferred" or "especially preferred" compositions, are particularly useful as absorbents in absorbent structures and articles. Such hydrogel-forming polymer materials having the characteristics hereinbefore described can be prepared by reacting conventional monomers and cross-linking agents while appropriately controlling such reaction conditions as concentration and type of the monomers, cross-linking agents and/or initiators used; polymerization temperature; nature of the reaction medium; and procedures used for polymer recovery and/or drying. It has furthermore been discovered that the particular combination of gel volume, gel strength and extractable polymer content values which characterizes the "preferred" and "especially preferred" polymer compositions hereinbefore described can be realized by preparing such "preferred" or "especially preferred" compositions in a certain specific manner as hereinafter described.

The first step in the process for preparing the preferred and especially preferred hydrogel-forming polymer compositions of this invention comprises the preparation of an aqueous reaction mixture in which to carry out polymerization to form the desired polymer materials. One essential element of such a reaction mixture is, of course, the acid group-containing monomer material which will form the backbone of the hydrogel-forming polymers to be produced. The reaction mixture will generally comprise from about 5% to 35% by weight, more preferably from about 8% to 24% by weight, of such polymerizable, unsaturated, acid group-containing monomers of the type hereinbefore described. Such monomer concentrations are generally somewhat below those which have heretofore been commonly utilized to prepare hydrogel-forming polymers of the same general type as those of this invention. Utilization of such reltively low monomer concentrations is believed to be one factor which serves to minimize the extractable polymer content of the resulting hydrogel-forming polymer materials.

Another factor which also appears to favor preparation of preferred and especially preferred polymer compositions having the requisite high gel volume, high gel strength and low extractable polymer content characteristics relates to polymerization using acid group-containing monomers in their free acid form. Prior art hydrogel synthesis procedures, for example those disclosed in the hereinbefore referenced U.S. Pat. Nos. 4,286,082 and 4,340,706, prefer that mixtures of free acid monomers and their salts be utilized for synthesis of hydrogel-forming polymers. In accordance with the present invention, however, substantially all of the unsaturated, acid group-containing monomers in the aqueous reaction mixture must be polymerized in their free acid, unneutralized form.

Another essential component of the aqueous reaction mixture used to prepare the preferred and especially preferred hydrogel-forming polymer compositions herein comprises a cross-linking agent of the type hereinbefore described. The cross-linking agent will generally be present in the aqueous reaction mixture in an amount of from about 0.001 mole percent to 5 mole percent based on total moles of monomer present in the aqueous mixture. More preferably, the cross-linking agent comprises from about 0.01 mole percent to 3 mole percent of total monomer present in the aqueous reaction mixture.

An optional component of the aqueous reaction mixture used to prepare the hydrogel-forming polymer compositions herein comprises a free radical initiator. Such an initiator may be any conventional water-soluble polymerization initiator material including, for example, peroxygen compounds such as sodium, potassium and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate and the like. Conventional redox initiator systems can also be utilized. Such systems are formed by combining the foregoing peroxygen compounds with reducing agents such as sodium bisulfite, L-ascorbic acid or ferrous salts. If utilized, the initiator material can comprise up to about 5 mole percent based on the total moles of polymerizable monomer present. More preferably the initiator comprises from about 0.001 to 0.5 mole percent based on the total moles of polymerizable monomer in the aqueous reaction mixture.

In one preferred embodiment of the hydrogel-forming polymer synthesis process herein, polymers of especially low extractable polymer content can be realized by utilizing in the aqueous reaction mixture no more than the minimum effective amount of initiator necessary to promote polymerization. One method for achieving such controlled minimum utilization of initiator is to incrementally add to the aqueous reaction mixture only that amount of the initiator, or component thereof, which is sufficient to initiate and sustain polymerization. For example, one component of a two-component redox initiator system may be premixed into the aqueous reaction mixture, and the other component can then be added incrementally in amounts sufficient to promote complete polymerization of the acid-containing monomers and cross-linking agent. Utilization of minimum initiator concentration in the context of preparation of water-soluble polymer materials is described in detail in Login et al.; U.S. Pat. No. 4,473,689; issued Sept. 25, 1984, incorporated herein by reference. Use of the minimum initiator concentration in the instant invention is an analagous procedure to that described in this '689 patent, and such a procedure can be used to prepare those substantially water-insoluble, hydrogel-forming polymers of the present invention which contain very low levels of extractable polymer material.

Other optional components of the aqueous reaction mixture used in the process for preparing the preferred and especially preferred hydrogel-forming polymer compositions herein comprise the various non-acidic comonomer materials hereinbefore described. Such optional comonomers can comprise, for example, esters of the essential unsaturated acidic functional group-containing monomers or other comonomers containing no carboxyl or sulfonic acid functionalities at all. Generally the aqueous reaction mixture will contain no more than about 50 mole percent based on total monomer present of these optional non-acid comonomers, and preferably no more than about 25 mole percent. As noted, hereinbefore, however, one type of non-acid comonomer which must not be present in the aqueous reaction mixture to any significant extent are monomers containing acid salt groups.

Since the objective of the present synthesis process is to prepare hydrogel-forming polymer compositions which are substantially free of graft polymerized polymer moieties, the aqueous reaction mixture used to prepare the hydrogels herein should likewise be substantially free of graft polymerizable polymer moieties. Thus, the aqueous reaction mixture should contain no materials such as starch or cellulose which are two polysaccharides typically used to prepare some types of known hydrogel-forming polymer materials.

In a second essential step of the polymer preparation process herein, the aqueous reaction mixture is subjected to polymerization conditions which are sufficient to produce in said mixture those water-insoluble, slightly cross-linked polymer materials which produce or would produce, upon subsequent neutralization to a degree of neutralization of at least about 50% and upon subsequent drying, hydrogel-forming polymers having the gel volume, gel strength, and extractable polymer content characteristics hereinbefore described for the preferred class of hydrogel-forming polymer materials. Such polymerization conditions will generally involve a polymerization temperature of from about 0° C. to 100° C., more preferably from about 5° C. to 40° C. Temperatures within the preferred range are generally somewhat lower than those which have been conventionally utilized to prepare hydrogel-forming materials of this same general type. Use of such lower temperatures may tend to promote the preparation of material having relatively low levels of extractable polymers.

Polymerization conditions under which the aqueous reaction mixture herein is maintained can also include, for example, subjecting the reaction mixture, or portions thereof, to any conventional form of polymerization activating irradiation. Use of radioactive, electronic, ultraviolet or other electromagnetic radiation is a conventional polymerization technique and can be employed in the present invention in those instances wherein little or no initiator materials are used.

A third essential step in the polymer preparation process herein involves the neutralization of the acid functional groups of the polymers formed in the aqueous reaction mixture. Neutralization can be carried out in any conventional manner which results in at least about 25 mole percent, and more preferably at least about 50 mole percent, of the total monomers utilized to form the polymer being acid group-containing monomers that are neutralized with a salt-forming cation. Such salt-forming cations include, for example, alkali metal, ammonium, substituted ammonium and amine. Since polymerization must take place as hereinbefore described using the essential monomers in their free acid form, neutralization must necessarily be carried out after the polymerization reaction is substantially complete and after the polymer materials have substantially been formed.

An additional optional process step which can be, and usually will be, utilized in connection with the polymer preparation process herein involves drying and recovery of hydrogel-forming polymer material. The polymer material formed in the reaction mixture, either before or after neutralization, can be dried by any conventional method. Thus polymer in the aqueous reaction mixture can be directly dried by subjecting the mixture or the polymer recovered from the mixture to temperatures of from about 40° C. to 150° C. for a period of time sufficient to form a semi-solid mass of material. Care should be taken to avoid subjecting the polymer material being dried to excessive elevated temperatures which tend to break cross-links and which can thereby adversely affect gel strength and extractables characteristics.

Alternatively, water can be removed from the reaction mixture by azeotropic distillation. In such a procedure an azeotrope-forming solvent such as cyclohexane is combined with the gelled mass of polymer material, and the temperature of the resulting mixture is maintained at or above the boiling point of the resulting azeotrope. In yet another drying procedure the polymer-containing aqueous reaction mixture can be treated with a dewatering solvent such as methanol. Combinations of these drying procedures may also be utilized.

The dewatered mass of polymer can be chopped or pulverized to form particles of the dried hydrogel-forming polymer material. Such hydrogel-forming polymer particles can be utilized as absorbents in absorbent structures and articles as hereinafter more fully described.

Frequently the hydrogel-forming polymer preparation process of this invention will be carried out using an aqueous solution polymerization procedure. In such a solution polymerization procedure, water-miscible solvents and/or other compatible optional ingredients such as surfactants can be added to the aqueous reaction mixture. In such procedures, the aqueous reaction mixture will be generally maintained as a single-phase system until solid particles of polymer are formed.

It is also possible, however, to carry out the polymerization process using multi-phase polymerization processing techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent such as cyclohexane. Polymerization in such procedures still occurs in the aqueous phase, but suspensions or emulsions of this aqueous phase in an organic solvent permits better control of the exothermic heat of polymerization and further provides the flexibility of adding one or more or the aqueous reaction mixture components in a controlled manner to the organic phase.

Inverse suspension polymerization procedures are described in greater detail in Obayashi et al.; U.S. Pat. No. 4,340,706; Issued July 20, 1982 and in Flesher et al.; U.S. Pat. No. 4,506,052; Issued Mar. 19, 1985. Both of these patents are incorporated herein by reference. As noted in those patents, when inverse suspension polymerization or inverse emulsion polymerization techniques are employed, additional ingredients such as surfactants, emulsifiers, polymerization stabilizers and the like may be added to the overall reaction mixture. When inverse phase processes, or for that matter any other processes, employing organic solvent are utilized, it is important that the hydrogel-forming polymer material recovered from such processes be treated to remove substantially all of the excess organic solvent. It is highly preferred, for example, that the hydrogel-forming polymers herein contain no more than about 0.5% by weight of residual organic solvent.

It should also be noted that the description set forth hereinbefore concerning the composition of the aqueous reaction mixture applies to the overall polymerization reaction mixture if a substantially single-phase aqueous solution polymerization is utilized but applies only to the aqueous phase of the overall reaction mixture if two-phase inverse suspension or inverse emulsion polymerization techniques are employed. Thus, for purposes of the present invention, the term "aqueous reaction mixture" also means and applies to the aqueous phase of a two-phase overall or total reaction mixture.

The dried and neutralized improved hydrogel-forming polymer compositions herein, whether as broadly defined or whether of the "preferred" or "especially preferred" types as hereinbefore described, can be employed in conventional manner in combination with hydrophilic fiber material to form improved absorbent structures useful in absorbent articles. Frequently such absorbent structures will comprise combinations of hydrophilic fiber material and discrete particles of hydrogel-forming polymer material which has the gel volume, hydrogel gel strength and extractable polymer contact characteristics hereinbefore described.

Various types of hydrophilic fiber material can be used in the absorbent structures of this invention. Any type of hydrophilic fiber which is suitable for use in conventional absorbent products is also suitable for use in the absorbent structures herein. Specific examples of such fibers include cellulose fibers, rayon, and polyester fibers. Other examples of suitable hydrophilic fibers are hydrophilized hydrophobic fibers, such as surfactant-treated or silica-treated thermoplastic fibers. For reasons of availability and cost, cellulose fibers, in particular wood pulp fibers, are preferred. The absorbent structures of this invention will generally comprise from about 50% to 98% by weight, and more preferably from about 65% to 90% by weight of hydrophilic fiber material.

As indicated, the improved hydrogel-forming polymer material as hereinbefore described can be employed in the absorbent structures of this invention in the form of discrete particles. Such hydrogel-forming polymer particles can be of any desired shape, e.g., spherical or semi-spherical, cubic, rod-like, polyhedral, etc. Shapes having a large greatest dimension/smallest dimension ratio, like needles, flakes and fibers, are also contemplated for use herein. Agglomerates of hydrogel-forming polymer particles may also be used.

Although the absorbent polymer-containing structures herein are expected to perform well with hydrogel-forming particles having a particle size varying over a wide range, other considerations may preclude the use of very small or very large particles. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption is affected by particle size. Larger particles have very much reduced rates of absorption. Preferred for use herein are hydrogel-forming particles having an average particle size of from about 50 microns to about 1 mm. "Particle Size" as used herein means the weighted average of the smallest dimension of the individual particles.

The amount of hydrogel-forming polymer particles used in the absorbent structures herein can be most conveniently expressed in terms of a weight percentage of the absorbent structure. Thus, the absorbent structures herein will generally contain from about 2% to 50%, more preferably from about 10% to 35%, by weight of the hydrogel-forming material. This concentration of hydrogel-forming material can also be expressed in terms of a weight ratio of hydrogel-forming polymers to hydrophilic fiber material. These ratios may range from about 2:98 to about 50:50. The optimum polymer/fiber ratio is in the range of from about 10:90 to about 35:65. Based on a cost/performance analysis, polymer/fiber ratios of from about 10:90 to about 25:75 are preferred for use in the absorbent structures herein.

The density of the absorbent structures herein can be of some importance in determining the absorbent properties of the structures and of the absorbent articles in which such structures are employed. The density of the absorbent structures herein will generally be in the range of from about 0.06 to about 0.3 g/cm$^3$, and more preferably within the range of from about 0.09 to about 0.18 g/cm$^3$. Typically the basis weight of the absorbent structures herein can range from about 0.02 to 0.12 gm/cm$^2$. Density values for these structures are calculated from basis weight and caliper. Caliper is measured under a "gentle" load of 10 grams/cm$^2$. Density and basis weight values include the weight of the hydrogel-forming particles.

In a preferred embodiment, the absorbent structures will comprise an intimate admixture of hydrophilic fiber material and hydrogel-forming particles with the hydrogel-forming particles being distributed, and preferably sustantially uniformly distributed, throughout a hydrophilic fiber matrix. Absorbent structures of this type can be formed by air-laying a dry mixture of hydrophilic fibers and hydrogel-forming particles and, if desired or necessary, densifying the resulting web. Such a procedure is described more fully in Procter & Gamble; European Patent Publication No. EP-A-122,042; published Oct. 17, 1984, incorporated herein by reference. As indicated in this patent application, the webs formed by this procedure will peferably comprise substantially unbonded fibers and will preferably have a moisture content of 10% or less.

Alternatively, the combination of hydrophilic fiber material and hydrogel-forming particles used as the absorbent structures herein can comprise a laminate containing at least one, and preferably two or more, layers of dispersed hydrogel-forming particles. The hydrogel-forming particle-containing laminates can be overwrapped with and separated by sheets of hydrophilic fiber material such as tissue paper if desired. Such laminate structures are more fully described in Kramer, Young and Koch; U.S. Ser. No. 563,339; filed Dec. 20, 1983, incorporated herein by reference.

Because of the unique absorbent properties of the hydrogels gormed from the improved polymer materials employed therein, the absorbent structures of this invention are very suitable for use in absorbent articles, and especially disposable absorbent articles. By "absorbent article" herein is meant a consumer product which is capable of absorbing significant quantities of water and other fluids (i.e., liquids), like body fluids. Examples of absorbent articles include disposable diapers, sanitary napkins, incontinence pads, paper towels, facial tissues, and the like. As compared to conventional hydrophilic fibrous webs, the absorbent structures of this invention have a high absorbent capacity. Thus, these absorbent structures are particularly suitable for use in articles like diapers, incontinent pads, and sanitary napkins.

Absorbent articles herein will in general comprise a liquid impervious backing sheet, a liquid pervious, relatively hydrophobic topsheet and an absorbent core comprising the absorbent structure of the present invention positioned between said backing sheet and said topsheet. Liquid impervious backing sheets can comprise any material, for example polyethylene or polypropylene having a caliper of about 1.5 mils, which will help retain fluid within the absorbent article. Relatively hydrophobic, liquid pervious topsheets can comprise any material such as polyester, polyolefin, rayon and the like which is substantially porous and permits a fluid to readily pass therethrough into the underlying absorbent structure.

Particularly preferred absorbent articles herein are disposable diapers. Disposable diapers comprising the absorbent structures of the present invention may be made by using conventional diaper making techniques, but by replacing or supplementing the wood pulp fiber web ("airfelt") core which is typically used in conventional diapers with an absorbent structure of the present invention. Articles in the form of disposable diapers are fully described in Duncan and Baker, U.S. Pat. No. Re 26,151, issued Jan. 31, 1967; Duncan, U.S. Pat. No. 3,592,194, issued July 13, 1971; Duncan and Gellert, U.S. Pat. No. 3,489,148, issued Jan. 13, 1970; and Buell, U.S. Pat. No. 3,860,003, issued Jan. 14, 1975; which patents are incorporated herein by reference. A preferred disposable diaper for the purpose of this invention comprises an absorbent core containing the absorbent structures of this invention; a topsheet superposed or co-extensive with one face of the core, and a liquid impervious backsheet superposed or co-extensive with the face of the core opposite the face covered by the topsheet. The backsheet most preferably has a width greater than that of the core thereby providing side marginal portions of the backsheet which extend beyond the core. The diaper is preferably constructed in an hourglass configuration.

One embodiment of a disposable diaper article according to the present invention is shown in the drawing. The hourglass-shaped diaper structure of the drawing comprises a liquid impervious backing sheet 101. Positioned on the top of the backing sheet 101 is an hourglass-shaped absorbent core 102 comprising the absorbent structure of the present invention. This core contains hydrophilic fiber material such as wood pulp fiber. Also distributed throughout the absorbent core 102 are discrete particles 103 of substantially water-insoluble, partially neutralized, substantially dry, hydrogel-forming polymer material which has the high gel volume, high hydrogel gel strength and low extractable polymer content characteristics hereinbefore described. Positioned on top of the hourglass-shaped absorbent core 102 is a liquid pervious topsheet 104.

In another embodiment of a disposable diaper article, the polymer-containing absorbent structure of the present invention is placed next to the diaper backsheet as an insert underneath an upper layer of the diaper core, which upper layer consists essentially of wood pulp fiber. The polymer-containing absorbent structure used as an insert can have the same size and shape as the wood pulp fiber layer of the core, or can be generally smaller. In a specific embodiment the wood pulp fiber layer is hour-glass shaped (i.e., the width at the center of the core is substantially less than the width at the ends), and the polymer-containing absorbent structure used as an insert is oblong and is positioned toward the front of the diaper article. In a similar embodiment, the hour-glass-shaped upper layer of the core may also contain small amounts, e.g., up to about 8% by weight, of hydrogel-forming material.

Because the absorbent structures of the present invention are highly absorbent, they are also quite suitable for use in sanitary napkins. As is the case with disposable diapers, sanitary napkins utilizing the present absorbent structures may be derived from conventional sanitary napkins by simply replacing the absorbent core thereof (typically a web of wood pulp fibers) with the polymer-containing absorbent structure of the present invention. Such replacement may be on a weight-by-weight basis, which results in a reduction in volume and a gain in capacity; or the replacement may be on a less than equal weight basis, thereby sacrificing part of the gain in absorbent capacity in favor of an even greater reduction in bulk. The absorbent structures used in sanitary napkins preferably have a caliper of from about 0.1 mm to about 2 mm, more preferably from about 0.3 mm to about 1 mm.

An example of a sanitary napkin comprises a pad of the absorbent structure of the present invention; a hydrophobic topsheet; and a fluid impervious bottom sheet. The topsheet and the backsheet are placed at opposite sides of the absorbent structure. Optionally, the absorbent structure is wrapped in envelope tissue. Suitable materials for top sheets, bottom sheets and envelope tissue are well known in the art. A more detailed description of sanitary napkins and suitable materials for use therein is found in Duncan and Smith, U.S. Pat. No. 3,871,378; issued Mar. 18, 1975, the disclosure of which is incorporated herein by reference.

The hydrogel-forming polymer compositions herein, processes for their preparation and absorbent structures and absorbent articles containing these hydrogel-forming materials are illustrated by the following examples:

TEST METHODS

In a number of the examples herein, hydrogel-forming polymer characteristics such as gel volume, gel strength as measured by shear modulus of the resulting hydrogel and content of extractable polymer material are set forth. Where reported, these characteristics are determined using the following test methods:

A. Gel Volume Determination

Gel volume in terms of grams of synthetic urine absorbed per gram of hydrogel-forming polymer is determined by swelling the polymer samples in several aliquots of synthetic urine. The amount of such synthetic urine actually absorbed by the hydrogel-forming polymer is determined by a procedure which involves use of a synthetic urine solution containing Blue Dextrin so that optical absorbence measurements can be used to calculate the amount of synthetic urine that is not taken up by the hydrogel which forms.

(a) Blue Dextrin Solution Preparation

A 0.03% Blue Dextrin (BD) solution is prepared by dissolving 0.3 parts of Blue Dextrin (Sigma D-5751) in 1000 parts of Synthetic Urine (SU) solution. Synthetic Urine is 15.0 parts of 1% Triton X-100, 60.0 parts of NaCl, 1.8 parts of $CaCl_2 \cdot 2H_2O$, and 3.6 parts of $MgCl_2 \cdot 6H_2O$, diluted to 6000 parts with distilled $H_2O$. The resulting solution has an absorbence of about 0.25 at its absorbence maximum of 617 nm.

(b) Hydrogel Equilibration

Aliquots of the hydrogel-forming polymer to be tested are swelled in (i) 20 parts of Synthetic Urine (SU) solution and (ii) 20 parts of Blue Dextrin (BD) solution. The suspension in the Blue Dextrin (BD) solution is prepared in duplicate. For most hydrogels, 0.1–0.2 parts of hydrogel-forming dried powder is required to give a sufficiently high spectrophotometer reading relative to the Blue Dextrin reference solution. One hour of equilibration at ambient temperature under gentle stir-bar stirring is sufficient for swelling equilibrium to be attained. After equilibration, a >3 ml aliquot of supernatant is separated from each gel suspension by decantation followed by centrifugation.

(c) Gel Volume Determination

The optical absorbency (ABS) of each supernatant is determined spectrophotometrically with an accuracy of 0.001 absorbence units. The Synthetic Urine solution is used as an ABS=0.0 reference. The absorbency of the supernatant from the synthetic urine suspension without Blue Dextrin should not exceed 0.01 A; higher values indicate scattering from residual hydrogel gel particles or residual additives, and further centrifugation is necessary. The absorbency of the Blue Dextrin supernatants should exceed the absorbency of the Blue Dextrin reference solution by at least 0.1 absorbance units. Absorbency values below this range indicate the need to adjust the amount of hydrogel-forming polymer used to prepare the gel suspension.

(d) Gel Volume Calculation

The Gel Volume of the hydrogel-forming polymer in gms/gm is calculated from (i) the weight fraction of the hydrogel-forming polymer in the gel suspension and (ii) the ratio of the excluded volume to the total volume of the suspension. Since Blue Dextrin is excluded from the hydrogel due to its high molecular weight, this ratio is related to the measured absorbencies. The following equation is used to calculate the gel volume:

$$\text{Gel Volume} = \frac{(\text{gms } BD \text{ Solution})}{(\text{gms hydrogel-forming polymer})} \times \left[ 1 - \frac{(ABS\ BD\ \text{solution})}{(ABS\ BD\ \text{supernatant} - ABS\ SU\ \text{supernatant})} \right]$$

B. Gel Strength/Shear Modulus Determination

Gel strength of the hydrogels formed from the polymer materials herein is quantified by means of determining the shear modulus of a sample of the swollen hydrogel. Shear modulus is determined using a stress rheometer which comprises a circular lower plate onto which the swollen hydrogel sample is placed. A truncated conical upper element having the same projected surface area as the area of the lower circular plate is positioned above the circular lower plate. This upper element is lowered into the mass of swollen hydrogel material on the circular lower plate and is positioned at the proper gap relative to the circular lower plate. This gap corresponds to the point at which an untruncated cone would contact the lower plate.

An oscillating torque (stress) is applied torsionally to the conical element, and the resulting angular displacement of the cone is determined as a function of the applied torque.

The sample being tested is swollen to its gel volume in the same type of synthetic urine utilized in the gel volume determination. Excess free synthetic urine is removed from the hydrogel sample by blotting, and approximately 1.5 cc of the swollen hydrogel material is placed in the gap between the lower circular plate and the upper conical element of the rheometer. This hydrogel mass is usually formed from an agglomeration of swollen hydrogel particles which have unswollen particle dimensions less than 710 microns. Spherical particles should be ground to form irregular shaped particles before testing.

Stress and strain measurements are taken under the following conditions:

| Parameter | Value |
|---|---|
| Type of Rheometer | Sangamo Visco-elastic Analyzer |
| Configuration | Oscillating Cone and Plate |
| Plate Radius | 2.5 cm |
| Cone Radius (Edge to vertex) | ~2.5 cm |
| Cone Angle* | 43.6 milliradians |
| Oscillation Frequency | 1.0 Hertz |
| Strain Amplitude | <2.5% |
| Sample Temperature | 21.4° C. |

*Angle between surface of the lower plate and the surface of the cone i.e. ($\pi/2$ - semi-vertical angle).

Under these conditions, an oscillatory torque (stress) is applied via the upper conical element to the swollen hydrogel. This results in an oscillatory response (strain) of the sample which is reflected by the magnitude of the angle through which the conical element rotates in response to the applied torque. The shear modulus of the hydrogel is calculated from the ratio of (i) the applied stress to (ii) the amplitude of the in-phase component of the resultant strain.

For the particular cone/plate geometry employed in this testing, the ratio of stress (g-cm) to strain (milliradians) is converted to shear modulus (dynes/$cm^2$) using the following formula:

$$\text{Shear Modulus} = \frac{3 \times 981 \times \text{Cone Angle} \times \text{Cos(Phase Angle)} \times \text{Torque}}{2 \times \pi \times \text{Plate Radius}^3 \times \text{Strain}}$$

wherein the cone angle and strain are expressed in units of milliradians, the plate radius in units of cm and torque in units of g-cm. For hydrogels, the phase angle is close to zero and so the cosine of the phase angle is taken as unity. The factor 981 is that which converts g-cm to dyne-cm. Thus $$\text{Shear Modulus (dynes/cm}^2) = 1308 \times \frac{\text{Torque (gm-cm)}}{\text{Strain (milliradians)}}$$

for the particular equipment used in this test method.

C. Extractable Polymer Content Determination

Depending upon the type of hydrogel-forming material involved, two different methods are used herein to calculate extractable polymer content. For carboxylic acid-based hydrogel-forming polymers a potentiometric procedure is used to determine extractables. For sulfonic acid-based hydrogel-forming polymers, a gravimetric procedure is employed. It should be noted that both of these procedures may provide results that include in the total amount of extractable material those extractable components in the hydrogel which are not polymeric. Therefore, if a given polymer sample is known or believed to contain significant amounts of non-polymeric extractable material, such non-polymeric extractable material should be removed from the analyte in conventional fashion before running the extractable polymer content determination hereinafter described.

(1) Carboxylic Acid-Based Hydrogel-Forming Polymers

Extractable polymer content of carboxylic acid-based hydrogel-forming material is determined by admixing the hydrogel-forming polymer with synthetic urine for a period of time sufficient to substantially approach equilibrium with respect to extraction of polymer material from the hydrogel which is formed. The hydrogel/urine mixture is allowed to settle and a portion thereof is filtered. An aliquot of this filtrate is then taken, and the free acid groups on the polymer material dissolved in this filtrate are titrated to pH 10 with base. All of the carboxylate groups are then titrated to pH 2.7 with acid. These titration data are then used to calculate the amount of extractable polymer in the hydrogel-forming polymer sample.

(a) Preparation of the Extractable Polymer-Containing Filtrate Samples 1. 0.40 to 0.41 g of hydrogel-forming polymer is accurately (to ± 0.1 mg) weighed into a 150 ml disposable beaker. If glass beakers are used, they must be acid washed prior to use. (Glassware should be washed three times with dilute HCl [conc. HCl diluted 1:4 with distilled water], then three times with distilled water. This procedure removes traces of detergents and other contaminants which would otherwise interfere with the titration.)
2. 75 ml of synthetic urine (hereinbefore described in the Gel Volume Determination section) are added.
3. Samples are slowly stirred for a period of time sufficient to reach equilibrium. Equilibrium is generally reached within 16 hours. If extractable polymer content is to be measured as a function of time, then 1, 6, and 16 hour periods are sufficient to define the extractables versus time curve.
4. Samples are allowed to settle for 15 minutes.
5. Using a 3 ml disposable syringe and 0.22 micron filters, enough solution is filtered so that a 20 ml aliquot can be taken.

(b) Titration Conditions

1. If the titrations are to be performed manually, great care must be taken to assure that equilibrium is reached after each addition of titrant.
2. A 20 ml aliquot of the filtrate is transferred to a 50 ml disposable beaker. If glass beakers are being used, they must be acid washed prior to use as noted hereinbefore.
3. The aliquot is titrated to pH 10 with 0.1N NaOH.
4. The aliquot is then back titrated to pH 2.7 with 0.1N HCl.
5. Steps 3 and 4 are performed on 20 ml of synthetic urine to obtain titration blanks for both steps of the titration.

(c) Calculations

1. The amount of polymerized acid moieties (e.g., acrylic acid) (in millimoles) in the supernatant aliquot ($M_a$) is given by:

$$M_a = (V_a - V_{ab}) \times N_a \text{ millimoles (mm)}$$

where:
$V_a$ = The volume (in ml) of acid required to titrate the aliquot to pH 10.
$V_{ab}$ = The volume (in ml) of acid required to titrate 20 ml of synthetic urine to pH 10.
$N_a$ = The normality (in meq/ml) of the acid (nominally 0.10 meq/ml)

2. The total amount of polymerized acid moieties (e.g. acrylic acid) plus polymerized neutralized acid moieties (e.g., sodium acrylate) (in mm) in the supernatant aliquot ($M_t$) is given by:

$$M_t = (V_b - V_{bb}) \times N_b \text{ millimoles}$$

where:
$V_b$ = The volume (in ml) of base required to titrate the aliquot from pH 10 down to pH 2.7.
$V_{bb}$ = The volume (in ml) of base required to titrate 20 ml of synthetic urine from pH 10 down to pH 2.7.
$N_b$ = The normality (in meq/ml) of the base (nominally 0.10 meq/ml).

3. The amount of polymerized neutralized acid moieties (e.g., sodium acrylate) (in mm) in the original supernatant aliquot ($M_b$) is given by:

$$M_b = M_t - M_a$$

4. The total amounts of polymerized acid moieties ($W_a$) and polymerized neutralized acid moieties ($W_b$) (e.g., acrylic acid plus sodium acrylate) extracted (in mg) are given by:

$$W_a = M_a \times E_a \times D \text{ and } W_b = M_b \times E_b \times D$$

where:
$E_a$ = The equivalent weight of acid moiety in polyacid moiety (e.g., acrylic acid in polyacrylic acid = 72 meq/mg).
$E_b$ = The equivalent weight of neutralized acid moiety in neutralized polyacid moiety (e.g., sodium acrylate in sodium polyacrylate = 94 meq/mg).
D = The dilution factor (75 ml/20 ml = 3.75).

5. The percent extractable polymer in the hydrogel-forming polymer sample (e) is given by:

$$e = [(W_a + W_b) \times 100]/W \text{ percent}$$

where: W = The sample weight in mg.

2. Sulfonic Acid-Containing Hydrogel-Forming Polymers

Extractable polymer content of sulfonic acid-based hydrogel-forming polymers is determined by a gravimetric procedure wherein hydrogel samples are swollen overnight in distilled water, and the polymer content in the filtrate is gravimetrically determined. By comparing extractable content determinations for carboxylic acid-based hydrogel-forming polymers, using both the potentiometric method hereinbefore described and the gravimetric method, it has been determined that the extractables readings given by the gravimetric method using distilled water overnight provides acceptable correlation with extractables determined by the 16-hour synthetic urine procedure used in the potentiometric method.

The particular procedure of the gravimetric extractables determination are set forth as follows:

Into a 500 ml Erlenmeyer flask is weighed accurately (to ± 0.1 mg) about 0.25 grams of dry hydrogel-forming polymer ($W_p$). 250 ml of distilled water is added, and the mixture is stirred slowly for 1 hour. After this hour has passed, stirring is stopped, and the swollen gel is allowed to settle overnight. In the morning enough of the supernatant is filtered using a 3 ml disposable syringe and 0.22 micron filter to obtain at least 40 ml of filtrate. Exactly 40 ml of filtrate is placed into a clean 100 ml round-bottomed flask, and the solution is concentrated on a rotary evaporator (water aspirator vacuum, bath temperature 55° C). The remaining 2–3 ml of solution is transferred quantitatively to a tared weighing vial with the aid of additional distilled water. The solution in the weighing vial is reduced to dryness in an oven at 120° C. The vial is cooled, reweighed, and the weight of residue ($W_r$) is determined using the tare weight of the vial. The percent extractable polymer (e) is calculated from the weight of dry polymer ($W_p$) and weight of residue ($W_r$) by the following equation.

$$e = \frac{W_r \times 250}{W_p \times 40} \times 100$$

As indicated, the extractables value obtained from this calculation is believed to approximately correspond to a 16-hour equilibrium extractables content value in synthetic urine.

EXAMPLE I

Four hundred and fifty parts of doubly distilled water were placed in a reaction vessel equipped with a mechanical stirrer, argon inlet, thermometer, and pressure-equalizing addition funnel containing 0.136 parts of N,N-methylenebisacrylamide dissolved in 92 parts of acrylic acid. The water and contents of the funnel were separately purged with argon through submerged gas dispersion tubes for 1 hour at 25° C. The water was then cooled to 10° C. while being vigorously stirred; 0.05 parts of ascorbic acid dissolved in 2 parts of water was added, immediately followed by 0.10 parts of a 30% hydrogen peroxide solution dissolved in 2 parts of water.

The contents of the addition funnel were then added to the solution. Within 5 minutes, the mixture formed a clear gel which could no longer be stirred. While maintaining external cooling at 6° C., the temperature of the gel rose to 30° C. after 30 minutes and then began to fall. The gel was then heated to a temperature of 40° C. for 3 hours. A portion of this gel (63.1 parts) was withdrawn from the flask and placed in a breaker containing 4.2 parts of sodium hydroxide dissolved in 80 parts of water.

The gel was chopped thoroughly until it had imbibed all of the surrounding fluid and was kept at 40° C. for 16 hours. The transparent, rubbery particles were then added to 500 parts of methanol at 40° C. and further chopped, converting them to opaque, sticky particles. The supernatant fluid was then removed, and 500 parts of fresh methanol were added and chopping was continued. A final decantation/addition/chopping produced hard particles which were stirred for 2 hours at 40° C. and then isolated by filtration. These particles were dried under high vacuum at 60° C. for 3 hours and pulverized to obtain 16.4 parts of a white powder.

Such powder had a gel volume of 59 g/g and an extractables content of 3.7%. The hydrogel formed from the powder had a shear modulus of $4.71 \times 10^3$ dynes/cm$^2$. Degree of neutralization was 70%.

Example II

Another portion of the neutralized gel particles prepared as in Example I (before treatment with methanol) was dried directly at 80° C. under high vacuum for 16 hours, pulverized, and redried for one hour. The resulting white powder has a gel volume of 45 g/g and an extractable content of 3.9%. The hydrogel formed from this powder had a shear modulus of $9.68 \times 10^3$ dynes/cm$^2$. Such a sample also has a degree of neutralization of 70%.

Example III

Four hundred and fifty parts of doubly distilled water, 92 parts of acrylic acid, and 1.87 parts of N,N'-methylenebisacrylamide were placed in a reaction vessel equipped with a mechanical stirrer, thermometer, and argon inlet. The solution was stirred at 25° C. and purged with argon through a submerged dispersion tube for 1 hour. The solution was then vigorously stirred and cooled to 11° C.; 0.025 parts of ascorbic acid dissolved in 2 parts of water, immediately followed by 0.050 parts of a 30% hydrogen peroxide, solution dissolved in 2 parts of water, were added. Within 3 minutes the mixture gelled and stirring was no longer possible. While maintaining external cooling at 2° C.–5° C., the reaction temperature rose to 16° C. after 30 minutes and then began to fall.

After heating the mixture to 40° C. for three hours, the brittle gel was broken up and ground in a mortar and pestle to give small rubbery particles. A solution of 35.4 parts of sodium hydroxide in 1200 parts of water was added to the particles. After thorough mixing, all excess fluid had been imbibed.

The resulting gel particles were kept at 40° C. for 16 hr. One portion of the gel particles was treated repeatedly with methanol and dried as described in Example I. After pulverization and an additional hour of drying, a white powder was obtained having a gel volume of 27 g/g and an extractables content of 0.4%. The powder forms a hydrogel having a shear modulus of $3.92 \times 10^4$ dynes/cm$^2$. Degree of neutralization was 70%.

Another portion of the gel particles was directly dried under high vacuum at 80° C. for 16 hours before grinding and for an additional one hour after drying to give a white powder having a gel volume of 26 g/g and an extractables content of 0.9%. This powder forms a hydrogel having a shear modulus of $4.58 \times 10^4$ dynes/cm$^2$. Degree of neutralization was also 70%.

EXAMPLE IV

A polymerization was carried out using the amounts of materials and methods of Example I, except that 0.748 parts of N,N'-methylenebisacrylamide were used. The final white powder has a gel volume of 37 g/g and an extractables content of 0.7%. The hydrogel formed from the powder has a a shear modulus of $1.95 \times 10^4$ dynes/cm$^2$. Degree of neutralization was 70%.

EXAMPLE V

A polymerization was carried out using the amounts of materials and methods of Example I, except that 0.374 parts of N,N'-methylenebisacrylamide were used. The final white powder obtained has a gel volume of 48 g/g and an extractables content of 2.1%. The hydrogel formed from the powder had a a shear modulus of $1.11 \times 10^4$ dynes/cm$^2$. Degree of neutralization was 70%.

EXAMPLE VI

A polymerization was carried out using the amounts of materials and methods of Example V, except that 0.025 parts of ascorbic acid dissolved in 2 parts of water and 0.050 parts of a 30% hydrogen peroxide solution dissolved in 2 parts of water were used as the initiator system. The final white powder that was obtained has a gel volume of 46 g/g and an extractables content of 1.1%. The hydrogel formed from this powder had a shear modulus of $9.94 \times 10^3$ dynes/cm$^2$. Degree of neutralization was 70%.

EXAMPLE VII

Four hundred and forty parts of doubly distilled water, 92 parts of acrylic acid, and 0.374 parts of N,N'-methylenebisacrylamide were placed in a reaction vessel equipped with a mechanical stirrer, thermometer, argon inlet, and pressure-equalizing addition funnel. The contents of the flask were stirred gently while being purged with argon through a submerged dispersion tube for 1 hour at 25° C. Half-way through this purge, the addition funnel was charged with 0.050 parts of a 30% hydrogen peroxide solution dissolved in 9 parts of water; this solution was also similarly purged with argon. After the purge period, the stirring rate was increased slightly, and the solution temperature was equilibrated with that of an exterior cooling bath at 12° C.

In a slow, dropwise manner, a portion of the contents of the addition funnel was added until a 0.25° C. reaction temperature rise coupled with a noticeable viscosity increase appeared. This occurred after about 2 parts of the hydrogen peroxide solution had been added in 13 minutes. Shortly thereafter, stirring was no longer possible. After 90 minutes, the gel reaction temperature reached a maximum of 22° C. and began to fall.

At this time the gel was heated to 40° C. for three hours. A portion of this gel (69.9 parts) was withdrawn and added to a solution of 4.93 parts of sodium hydroxide in 80 parts of water. The gel was chopped thoroughly until it had imbibed all of the surrounding fluid. It was then left at 40° C. for 16 hours.

Treatment of the resulting rubbery particles with methanol, drying, and pulverizing by the method of Example I gave 20.1 parts of a white powder. A portion of this powder was pulverized further and dried for an additional 1 hour to give a material having a gel volume of 47 g/g and an extractables content of 0.9%. The hydrogel formed from this material has a shear modulus of $1.11 \times 10^4$ dynes/cm$^2$. Degree of neutralizaton was 70%.

When a portion of the neutralized rubbery particles was directly dried under high vacuum at 80° C. for 16 hours (no methanol treatment) followed by the same pulverization and redrying, a white powder was obtained having a gel volume of 45 g/g and an extractables content of 2.2%. This powder forms a hydrogel having a shear modulus of $1.24 \times 10^4$ dynes/cm$^2$. Degree of neutralization was also 70%.

This example illustrates that hydrogel-forming materials of especially, low extractables content can be prepared using the minimum initiator concentration technique.

EXAMPLE VIII

A polymerization was carried out using the amounts of materials and methods of Example I except that 0.725 parts of trimethylol propane triacrylate were used in place of N,N'-methylenebisacrylamide. The final white powder that was obtained has a gel volume of 41 g/g and an extractables content of 2.1% The hydrogel formed from this powder has a shear modulus of $1.35 \times 10^4$ dynes/cm$^2$. Degree of neutralization was 70%.

EXAMPLE IX

Four hundred fifty parts of doubly distilled water, 92 parts of acrylic acid, and 0.748 parts of N,N'-methylenebisacrylamide were placed in a reaction vessel equipped with a mechanical stirrer, thermometer, and argon inlet. The solution was stirred at 25° C. and purged with argon by submerged dispersion tube for 1 hour. The temperature of the solution was raised to 64° C., the stirring speed was increased, and 0.051 parts of potassium persulfate dissolved in 3 parts of water were added.

Within 45 seconds, the solution had gelled, and stirring was no longer possible. While maintaining the external temperature at 65° C., the reaction temperature rose to 84° C. after 19 minutes and then began to fall. After maintaining the external temperature at 40° C. for three hours, 123.4 parts of this gel were chopped in the presence of 8.12 parts of sodium hydroxide dissolved in 160 parts of water. When all excess fluid had been imbibed, the resulting rubbery particles were left at 40° C. for 16 hours. These particles were dried and ground without methanol in the manner of Examples VII.

A white powder having a gel volume of 41 g/g and an extractables content of 3.9% was obtained. The hydrogel formed from this powder had a shear modulus of $1.43 \times 10^4$ dynes/cm$^2$. The degree of neutralization was about 70%.

EXAMPLE X

Three hundred sixty three parts of doubly distilled water, 187 parts of acrylic acid, and 0.080 parts of N,N-methylenebiacrylamide were dissolved and purged as in Example IX. To the quickly stirred solution cooled to 10° C. were added 0.05 parts of ascorbic acid dissolved in 3 parts of water quickly followed by 0.100 parts of hydrogen peroxide solution dissolved in 3 ml of water.

After 45 seconds, the reaction mixture had gelled and could no longer be stirred. Within 17 minutes, the reaction temperature had increased to 65° C. while maintaining external cooling below 10° C. When the temperature had fallen to 40° C., it was maintained there for 3 hours. A portion of the resulting extremely tough, rubbery gel (60.1 parts) was chopped in the presence of 7.9 parts of sodium hydroxide dissolved in 160 parts of water. It was left at 40° C. for 16 hours.

After drying and grinding as in Example IX, a white powder having a gel volume of 38 g/g and extractables content of 9.0% was obtained. The hydrogel formed from this powder had a shear modulus of $1.24 \times 10^4$ dynes/cm$^2$. Degree of neutralization was about 70%.

EXAMPLE XI

Five hundred forty parts of doubly distilled water, 60 parts of acrylic acid, and 1.22 parts of N,N'-methylenebisacrylamide were dissolved and purged as in Example X. To the quickly stirred solution cooled to 14° C. were added 0.02 parts of ascorbic acid dissolved in 3 parts water followed by 0.04 parts of hydrogen peroxide solution dissolved in 3 parts water. After 7 minutes, the viscosity of the solution prevented further stirring. After 114 minutes, the reaction temperature reached a high point of 17° C. and began to fall. The gel was then heated at 40° C. for three hours. A portion (113.2 parts) of the resulting brittle gel was broken up into small particles in a mortar and pestle and treated with 4.39 parts of sodium hydroxide dissolved in 80 parts of water.

After standing at 40° C. for 16 hours, the particles were dried and ground as in Example X to give a white powder having a gel volume of 43 g/g and an extractables content of 0.6%. The hydrogel formed from this powder had a shear modulus of $1.31 \times 10^4$ dynes/cm$^2$. Degree of neutralization was about 70%.

EXAMPLE XII

Four hundred and fifty parts of doubly distilled water, 92 parts of acrylic acid, and 0.040 parts of N,N'-methylenebisacrylamide were placed in a reaction vessel equipped with a mechanical stirrer, thermometer, and argon inlet. The solution was stirred at 25° C. and purged with argon by submerged dispersion tube for 1 hour. The stirring speed was then increased, and the solution temperature was lowered by external cooling to 11.8° C. 0.025 parts of ascorbic acid dissolved in 2 parts of water were added. A solution of 0.052 parts of 30% hydrogen peroxide in 9 parts of water were placed in an addition funnel and added drop by drop to the stirred reaction mixture. When six drops had been added, a viscosity increase was noted, and the addition was terminated Within 3 minutes, stirring was stopped, and after 41 minutes the reaction temperature reached 23° C. and then began to fall. At this time the reaction mixture was heated at 40° C. for 3 hours.

A portion of this gel (118 parts) was thoroughly chopped in the presence of 7.74 parts of sodium hydroxide dissolved in 160 parts in water until all excess fluid had been imbibed. The resulting rubbery particles were kept at 40° C. for 16 hours and then treated with methanol and dried in the manner of Example I. A white powder was obtained which has a gel volume of 74 g/g and an extractables content of 13%. The hydrogel formed from this powder had a shear modulus of $3.27 \times 10^3$ dynes/cm$^2$. Degree of neutralization was about 70%.

EXAMPLE XIII

This example illustrates preparation of a polyacrylate hydrogel-forming material using an inverse suspension polymerization technique.

A four-neck, 1 liter round-bottom resin kettle equipped with a stirrer, a reflux condenser, a dropping funnel, and an inert gas dispersion tube was charged with 430 ml of cyclohexane and 2.57 g of ethyl cellulose (Aldrich Chemical Company, Inc., ethoxyl content 48%). Argon gas was blown into the flask to purge dissolved oxygen, and the temperature elevated to 65° C. In a separate flask, 28.0 g of acrylic acid was dissolved in 111.8 g of distilled water. The monomer concentration in the aqueous phase was 20% by weight. Then, 0.0128 g of potassium persulfate and 0.1798 g of N,N'-methylenebisacrylamide were dissolved in the aqueous solution, and argon was introduced into the solution to remove oxygen present therein.

The contents of the latter flask were added dropwise to the contents of the above mentioned four-neck flask over a period of one-half hour. After completion of the dropwise addition, reaction was carried out at 65° C. for four hours, and then the reaction mixture was cooled to ambient temperature. Separately, in a flask, 23.2 g of 50.2% (w/w) sodium hydroxide solution is dissolved in 8.8 g distilled water and added dropwise to the contents of the four-neck flask. Following complete addition, the contents of the flask are allowed to stir for 20 minutes before the swollen polymer was isolated by filtration, allowed to stand overnight and then dried under reduced pressure at 80° C. to obtain spherical particles of a polymer product with gel volume, v, of 34 g/g, a hydrogel shear modulus of 21,300 dynes/cm$^2$ and extractables, e, of 3.5%. Degree of neutralization was 75%. The value for (0.23v−3.0) is 4.82 which is greater than the 3.5% value for e.

EXAMPLE XIV (Comparative)

This example also illustrates preparation of a polyacrylate-type hydrogel-forming material using an inverse suspension polymerization technique. In this example, however, a monomer concentration above that used in the process of the present invention is employed. Furthermore, the monomer used was 75% neutralized (sodium acrylate) instead of being predominantly in the free acid form as required by the process of the present invention.

In this example the same polymerization vessel as used in Example XIII was charged with 470 ml of cyclohexane and 2.80 g ethyl cellulose. Inert gas was introduced to expel dissolved oxygen therefrom, and the temperature raised to 65° C. In a separate flask, 57.0 g acrylic acid was neutralized with 47.3 g of 50.2% (w/w) sodium hydroxide solution dissolved in 54.9 g distilled water while externally cooling the charge. The monomer concentration in the aqueous phase was 44% by weight. Then, 0.0260 g potassium persulfate and 0.0073 g N,N'-methylenebisacrylamide were dissolved in the aqueous solution, and argon was blown into the solution to remove dissolved oxygen.

The contents of the latter flask were added dropwise over a period of one-half hour to the aforementioned four-neck flask, after which reaction was carried out at 65° C. for four hours before temperature was returned to ambient.

The polymer is isolated in a swollen state by filtration and dried under reduced pressure at 80° C. to yield spherical particles of polymer having a gel volume, v, of 35 g/g, a hydrogel shear modulus of 11,800 dynes/cm$^2$, and extractables, e, of 10.3%. (Some characteristics of the polymer were determined as an average of several runs.) The degree of neutralization was 75%. The value for (0.23v−3.0) is 5.05 which is not greater than the 10.3% value for e. Thus, this example illustrates the importance of utilizing acid form monomer at relatively low concentration if "preferred" hydrogel-forming material of especially low extractables is to be realized.

EXAMPLE XV

This example illustrates a reverse suspension polymerization procedure wherein water is removed from the polymer by azeotropic distillation prior to neutralization of the polymer.

A four-neck, 1 liter round bottom resin kettle equipped with a stirrer, a reflux condenser, a dropping funnel, and an inert gas-dispersion tube was charged with 430 ml cyclohexane and 2.57 g ethyl cellulose (Aldrich Chemical Company, Inc., ethoxyl content 48%). Argon gas was blown into the flask to purge dissolved oxygen, and the temperature elevated to 65° C. In a separate flask, 28.0 g acrylic acid was dissolved in 111.9 g distilled water. The monomer concentration in the aqueous monomer solution was 20% (water content: 80%). Then, 0.0064 g of potassium persulfate and 0.0599 g N,N'-methylenebisacrylamide were dissolved in the aqueous solution, and argon was introduced to remove oxygen therein. The resulting monomer solution was fed dropwise to the four-necked flask in an argon atmosphere in the course of 0.75 hours to effect polymerization and was subsequently held at 65° C. for four hours to complete the polymerization.

Thereafter, the water content of the polymer suspended in cyclohexane was adjusted to 55% by azeotropic distillation. The polymer beads were isolated by filtration and resuspended in 450 ml of fresh cyclohexane at ambient temperature. Separately, in a flask, 23.2 g of 50.2% (w/w) sodium hydroxide solution is dissolved in 87.4 g distilled water and the resulting solution is added dropwise over a period of 0.5 hours to the polymer suspended in cyclohexane. Following complete addition, neutralization is continued for 1.5 hours before the swollen polymer is isolated by filtration and dried under reduced pressure at 80° C. to obtain spherical beads of polymer product with a gel volume of 51 g/g, a hydrogen shear modulus of 7,570 dynes/cm$^2$, and extractables of 4.8%. The degree of neutralization of the material was 75%. Some characteristics of the polymer were determined as an average of several runs.

EXAMPLE XVI

This example illustrates the preparation of a sulfonic acid-containing polymer which forms a hydrogel having the characteristics of those of the present invention by virtue of the use of free acid monomers in relatively low concentrations.

A 4-necked, 1-liter round-bottomed resin kettle equipped with a stirrer, a reflux condenser, a jacketed dropping funnel, and an inert gas dispersion tube was charged with 510 ml of cyclohexane and 3.06 g ethyl cellulose (Aldrich Chemical Co., Inc., ethoxyl content 48%). Argon gas was introduced to expel dissolved oxygen, and the temperature was elevated to 65° C.

In a cooled flask, 25.2 g of acrylic acid was dissolved in 132.8 g of distilled water, to which was added 0.0128 g of potassium persulfate and 0.1797 g N,N'-methylenebisacrylamide. Then 8.0538 g of 2-acrylamido-2-methylpropane sulfonic acid (Lubrizol special process reaction grade II) was added to the aqueous solution, and argon was blown into the solution to remove oxygen present therein. The monomer concentration in the aqueous phase was 20% by weight. The contents of this flask were added from the cooled addition funnel dropwise over a period of about one-half hour to the contents of the aforementioned 4-necked kettle.

After completion of the dropwise addition, reaction was carried out at 65° C. for 4 hours, and then the reaction mixture was cooled to ambient temperature. Separately, in a flask, 23.2 g of 50.2% (w/w) NaOH solution was dissolved in 127.8 g of distilled water and added dropwise over the course of an hour to the contents of the 4-necked kettle. Following complete addition, the contents of the kettle were allowed to stir for 4 hours before the swollen polymer was isolated by filtration and dried under reduced pressure at 80° C. to obtain spherical particles of 75% neutralized polymer. This polymer has a gel volume of 38 g/g, extractables of 11% and a hydrogel shear modulus of 13,100 dynes/cm$^2$. Some characteristics of the polymer were determined as an average of several runs.

EXAMPLE XVII (Comparative)

This example illustrates preparation of a sulfonic-acid-containing polymer which forms a hydrogel having a higher extractables content than the hydrogels formed from polymers of this invention. Such high extractable materials result from the polymerization of sodium salt monomers in relatively high concentration.

The same polymerization vessel as in Example XVI was charged with 475 ml hexanes and 3.75 g SPAN 60 surfactant (sorbitan monostearate). Inert gas was introduced to expel dissolved oxygen therefrom, and the temperature was raised to 40° C.

In a separate flask, 51.3 g of acrylic acid was neutralized with 41.1 g of 50% (w/w) NaOH solution dissolved in 47.9 g distilled water while externally cooling the charge. Following neutralization, 35.1 g of 51.6% (w/w) sodium 2-acrylamido-2-methylpropane sulfonate solution was added along with 0.0074 g N,N'-methylenebisacrylamide and 0.0260 g potassium persulfate. The monomer concentration in the aqueous phase was 46% by weight. Argon gas was blown into the aqueous phase to remove any dissolved oxygen. The contents of the latter flask were added dropwise over a period of one-half hour to the four-necked kettle, after which reaction was carried out at 65° for 3 hours before the temperature was allowed to return to ambient. The swollen polymer was isolated by filtration and dried at 80° C. under reduced pressure to yield spherical particles of a 75% neutralized polymer product. This polymer has a gel volume of 35 g/g, extractables of 49% and a hydrogel shear modulus of 9,460 dynes/cm$^2$. Some characteristics of the polymer were determined as an average of several runs.

EXAMPLE XVIII

A disposable diaper is prepared comprising a polypropylene topsheet, two tissue plys, an absorbent core, a liquid impervious polyethylene backing sheet containing elastic leg bands along each side of the completed diaper and two tape fasteners. The absorbent core is an hourglass-shaped mixture of wood pulp fibers (airfelt) and particles of a water-insoluble, slightly cross-linked, partially neutralized, substantially dry hydrogel-forming polymer of this invention. The diaper is hand assembled using double-sided tape to fasten the individual components together. The diaper core is described in greater detail in the following Table I:

TABLE I

| Feature | Value |
| --- | --- |
| Core shape | Hourglass |
| Hydrogel-forming polymer | Polyacrylate of Example 1 |
| Airfelt concentration | 85% by weight |
| Hydrogel-forming polymer concentration | 15% by weight |
| Total surface area | 93.6 in.$^2$ (604 cm$^2$) |
| Crotch area | 46 in.$^2$ (297 cm$^2$) |
| Basis weight of crotch | 1.64 g/in.$^2$ (0.254 g/cm$^2$) |
| Core weight | 33.0 grams |

Such a diaper article is especially effective with respect to total fluid capacity and low incidence of diaper failure.

EXAMPLE XIX

Disposable diapers containing partially (i.e., about 75%) neutralized, hydrogel-forming polymer absorbents of varying characteristics are prepared in a manner substantially similar to that described in Example XVIII. These diapers are tested by panels of fifty mothers over a ten-day period in comparison with a control diaper which is a commercially marketed disposable diaper product containing no absorbent hydrogel-forming polymer. Each panelist receives sixty diapers, thirty of the test diaper and thirty of the control.

Each of the two diaper types is tested for five days. Mothers are asked to keep diaries concerning the percentage of each diaper type which leaks and to provide an indication of their overall preference of diaper type. In tabulating results concerning the percentage of panelists having a preference for the test diapers, it should be noted that the percentage of mothers expressing no preference for either the test or control diaper was divided equally between the test and control diapers.

A description of the characteristics of the hydrogel-forming polymer used in the test diapers as well as test results are set forth in Table II.

those having significantly higher levels of extractables than the polymers of the present invention. Diapers with these two polymer types have a significantly higher incidence of leakage and are furthermore not significantly preferred by mothers over the control diaper.

What is claimed is:

1. A substantially water-insoluble, slightly cross-linked, partially neutralized, hydrogel-forming polymer composition consisting essentially of
    (a) from about 50 mole percent to 99.999 mole percent of polymerized unsaturated, polymerizable, acid group-containing monomers; and
    (b) from about 0.001 mole percent to 5 mole percent of a cross-linking agent;
wherein said composition has a degree of neutralization of at least about 25% and is substantially free of graft polymerizable polymer moieties; and further wherein said polymer composition, upon neutralization to a degree of neutralization of at least 50%, has or would have a gel volume of at least about 20 grams of synthetic urine per gram of hydrogel-forming polymer, a gel strength such that the hydrogel formed from said polymer exhibits a shear modulus of at least about 2000 dynes/cm$^2$, an initial extractable polymer content, after one hour in synthetic urine, of no more than about 7.5% by weight of hydrogel-forming polymer, and an equilibrium extractable polymer content, at equilibrium in synthetic urine, of no more than about 17% by weight of hydrogel-forming polymer.

2. A hydrogel-forming polymer composition according to claim 1 wherein
    (a) said composition has a degree of neutralization of at least about 50%;
    (b) said composition has a gel volume of from about 25 to 80 grams of synthetic urine per gram of hydrogel-forming polymer;
    (c) the hydrogel formed from said composition has a gel strength such that the hydrogel exhibits a shear modulus of from about 2500 to 92,000 dynes/cm$^2$;
    (d) said composition has an initial extractable polymer content, after one hour in synthetic urine, of no more than about 5% by weight of hydrogel-forming polymer; and
    (e) said composition has an equilibrium extractable polymer content, at equilibrium in synthetic urine, of no more than about 10% by weight of hydrogel-

TABLE II

| Hydrogel-Forming Polymer No. | Gel Volume (grams/grams) | Shear Modulus (dynes/cm$^2$) | 1-Hour Extractables (% by weight) | 16-Hour Extractables (% by weight) | % of Test Diaper Leaked | % of Control Leaked | Favorable Preference For Test Diaper (%) |
| --- | --- | --- | --- | --- | --- | --- | --- |
| 1. | 27.3 | 3.95 × 10$^4$ | 2.4 | 6.3 | 11 | 18 | 76 |
| 2. | 25.5 | 4.68 × 10$^4$ | 3.0 | 5.4 | 7 | 13 | 66 |
| 3. | 26.6 | 3.52 × 10$^4$ | 4.4 | 8.2 | 9 | 18 | 67 |
| 4. | 21.7 | 3.48 × 10$^4$ | 4.4 | 10.6 | NA | NA | 74 |
| 5. | 27.9 | 2.73 × 10$^4$ | 5.6 | 11.8 | 10 | 15 | 79 |
| 6. | 32.3 | 1.75 × 10$^4$ | 7.2 | 16.1 | 9 | 15 | 76 |
| 7. | 27.3 | 3.45 × 10$^4$ | 4.5 | 5.5 | 10 | 16 | 69 |
| 8. | 37.4 | 1.05 × 10$^4$ | 14.9 | 16.5 | NA | NA | 51 |
| 9. | 27.9 | 2.21 × 10$^4$ | 16.3 | 31.7 | 18 | 15 | 40 |

NA = Not Available

It can be seen from the Table II data that diapers containing hydrogel-forming polymers having the characteristics as set forth in the present invention generally had fewer instances of diaper leakage and were generally highly preferred by mothers in comparison with the control diaper. Diapers with Polymer Numbers 8 and 9, on the other hand, are those wherein the polymers are forming polymer.

3. A hydrogel-forming polymer composition according to claim 2 wherein
    (a) said acid-group containing monomers are selected from acrylic acid, methacrylic acid, and 2- acrylamido-2-methylpropane sulfonic acid, and combinations thereof; and (b) said cross-linking agent is selected from
(i) di- and polyvinyl compounds;
(ii) di- and polyesters of unsaturated mono- and polycarboxylic acids with polyols;
(iii) bisacrylamides;
(iv) carbamyl esters obtained by reacting polyisocyanates with hydroxyl group-containing monomers;
(v) di- and polyallyl ethers of the polyols;
(vi) di- and polyallyl esters of polycarboxylic acids;
(vii) esters of unsaturated mono- and polycarboxylic acids with mono-allyl esters of polyols; and
(viii) di- and triallyl amines 4. A substantially water-insoluble, slightly cross-linked, partially neutralized, hydrogel-forming polymer composition consisting essentially of:
(a) from about 75% to 99.99% mole percent of polymerized acrylic acid monomers; and
(b) from about 0.01% to 3% mole percent of a cross-linking agent selected from N,N'-methylenebisacrylamide, trimethylol propane triacrylate and triallyl amine;
wherein said composition has at least 50% of its acrylic acid groups neutralized with sodium cations and is substantially free of graft polymerized polymer moieties, and further wherein said polymer composition has a gel volume, v, of at least about 20 grams of synthetic urine per gram of hydrogel-forming polymer, a gel strength such that the hydrogel formed from said polymer exhibits a shear modulus, s, of at least about 2000 dynes/cm$^2$, an initial extractable polymer content, after one hour in synthetic urine, of no more than about 7.5% by weight of hydrogel-forming polymer, and an equilibrium extractable polymer content, e, at equilibrium in synthetic urine, of no more than about 17% by weight of hydrogel-forming polymer.

5. A hydrogel-forming polymer composition according to claim 4 wherein the relationship between gel volume, v, and equilibrium extractable polymer content, e, is defined by the equation: $e \leq 0.23v - 3.0$.

6. A hydrogel-forming polymer composition according to claim 4 wherein the relationship between gel volume, v, and equilibrium extractable polymer content, e, is defined by the equation: $e \leq 0.23v - 3.0$; and wherein the relationship between gel volume, v, and shear modulus, s, is defined by the equation:

$$\log s \geq -2.494 \log v + 8.090.$$

7. A substantially water-insoluble, slightly cross-linked, partially neutralized, hydrogel-forming polymer composition consisting essentially of
(a) from about 75 mole percent to 99.99 mole percent of polymerized unsaturated, polymerizable, acid group-containing monomers; and
(b) from about 0.01 mole percent to 3 mole percent of a cross-linking agent;
wherein said composition has a degree of neutralization of at least about 25% and is substantially free of graft polymerizable polymer moieties; and further wherein said polymer composition, upon neutralization to a degree of neutralization of at least 50%, has or would have a gel volume, v, of at least about 20 grams of synthetic urine per gram of hydrogel-forming polymer, a gel strength such that the hydrogel formed from said polymer exhibits a shear modulus, s, of at least about 2000 dynes/cm$^2$, an initial extractable polymer content, after one hour in synthetic urine, of no more than about 7.5% by weight of hydrogel-forming polymer, and an equilibrium extractable polymer content, e, at equilibrium in synthetic urine, of no more than about 17% by weight of hydrogel-forming polymer, and further wherein the relationship between gel volume, v, and equilibrium extractable polymer content, e, is defined by the equation: $e \leq 0.23v - 3.0$.

8. A hydrogel-forming polymer composition according to claim 7 wherein
(a) said composition has a degree of neutralization of at least about 50%;
(b) said composition has a gel volume of from about 25 to 80 grams of synthetic urine per gram of hydrogel-forming polymer;
(c) the hydrogel formed from said composition has a gel strength such that the hydrogel exhibits a shear modulus of from about 2500 to 92,000 dynes/cm$^2$;
(d) said composition has an initial extractable polymer content, after one hour in synthetic urine, of no more than about 5% by weight of hydrogel-forming polymer; and
(e) said composition has an equilibrium extractable polymer content, at equilibrium in synthetic urine, of no more than about 10% by weight of hydrogel-forming polymer.

9. A hydrogel-forming polymer composition according to claim 8 wherein
(a) said acid group-containing monomers are selected from acrylic acid, methacrylic acid, 2-acrylamido-2-methylpropane sulfonic acid, and combinations thereof; and
(b) said cross-linking agent is selected from N,N'-methylenebisacrylamide, trimethylol propane triacrylate, and triallyl amine.

10. A substantially water-insoluble, slightly cross-linked, partially neutralized, hydrogel-forming polymer composition consisting essentially of
(a) from about 75 mole percent to 99.99 mole percent of polymerized unsaturated, polymerizable, acid group-containing monomers; and
(b) from about 0.01 mole percent to 3 mole percent of a cross-linking agent;
wherein said composition has a degree of neutralization of at least about 25% and is substantially free of graft polymerizable polymer moieties; and further wherein said polymer composition, upon neutralization to a degree of neutralization of at least 50%, has or would have a gel volume, v, of at least about 20 grams of synthetic urine per gram of hydrogel-forming polymer, a gel strength such that the hydrogel formed from said polymer exhibits a shear modulus, s, of at least about 2000 dynes/cm$^2$, an initial extractable polymer content, after one hour in synthetic urine, of no more than about 7.5% by weight of hydrogel-forming polymer, and an equilibrium extractable polymer content, e, at equilibrium in synthetic urine, of no more than about 17% by weight of hydrogel-forming polymer, and further wherein the relationship between gel volume, v, and equilibrium extractable polymer content, e, is defined by the equation: $e \leq 0.23v - 3.0$;
and further wherein the relationship between gel volume, v, and gel strength as measured by shear modulus, s, is defined by the equation:

$$\log s \geq -2.494 \log v + 8.090.$$

11. A hydrogel-forming polymer composition according to claim 10 wherein
(a) said composition has a degree of neutralization of at least about 50%;
(b) said composition has a gel volume of at least about 25 to 80 grams of synthetic urine per gram of hydrogel-forming polymer;
(c) the hydrogel formed from said composition has a gel strength such that the hydrogel exhibits a shear modulus of from about 2500 to 92,000 dynes/cm$^2$;
(d) said composition has an initial extractable polymer content, after one hour in synthetic urine, of no more than about 5% by weight of hydrogel-forming polymer; and
(e) said composition has an equilibrium extractable polymer content, at equilibrium in synthetic urine, of no more than about 10% by weight of hydrogel-forming polymer.

12. A hydrogel-forming polymer composition according to claim 11 wherein
(a) said acid group-containing monomers are selected from acrylic acid, methacrylic acid, 2-acrylamido-2-methylpropane sulfonic acid, and combinations thereof; and
(b) said cross-linking agent is selected from N,N'-methylenebisacrylamide, trimethylol propane triacrylate and triallyl amine.

13. A process for preparing a substantially water-insoluble, slightly cross-linked, partially neutralized hydrogel or hydrogel-forming polymer material suitable for use in absorbent products, said process comprising
(a) preparing a reaction mixture consisting essentially of from about 5% to 35% by weight of unsaturated, polymerizable, acid group-containing monomers in the free acid form, from about 0.001 mole percent to 5 mole percent, based on moles of polymerizable monomers, of a cross-linking agent and from 0 mole percent to about 5 mole percent, based on the moles of polymerizable monomers, of a free radical initiator in an aqueous medium which is substantially free of graft polymerizable polymer moieties;
(b) subjecting said aqueous reaction mixture to polymerization conditions which are sufficient to produce therein a substantially water-insoluble, slightly cross-linked polymer material which, upon subsequent neutralization to a degree of neutralization of at least 50% and upon subsequent drying, has or would have, a gel volume, v, of at least about 20 grams of synthetic urine per gram of hydrogel-forming polymer, a gel strength such that the hydrogel formed from said polymer material exhibits a shear modulus, s, of at least about 2000 dynes/cm$^2$, an initial extractable polymer content, after one hour in synthetic urine, of no more than about 7.5% by weight of hydrogel-forming polymer, an equilibrium extractable polymer content, e, at equilibrium in synthetic urine, of no more than about 17% by weight of hydrogel-forming polymer; and a relationship between gel volume, v, and equilibrium extractable polymer content, e, defined by the equation: $e \leq 0.23v - 3.0$; and
(c) neutralizing at least a portion of the acid groups of the polymer material formed in the aqueous reaction mixture with salt-forming cations to form a partially neutralized polymer material having a degree of neutralization of at least about 25%.

14. A process according to claim 13 wherein
(a) the acid groups of the polymer material formed in the aqueous reaction mixture are neutralized with salt-forming cations to form a polymer material having a degree of neutralization of at least about 50%;
(b) said neutralized polymer material has a gel volume of from about 25 to 80 grams of synthetic urine per gram of hydrogel-forming polymer;
(c) said neutralized polymer material forms a hydrogel having a gel strength such that said hydrogel exhibits a shear modulus of about 2500 to 92,000 dynes/cm$^2$; and
(d) said neutralized polymer material has an initial extractable polymer content, after one hour in synthetic urine, of no more than about 5% by weight of hydrogel-forming polymer and an equilibrium extractable polymer content, at equilibrium in synthetic urine, of no more than about 10% by weight of hydrogel-forming polymer.

15. A process according to claim 14 wherein
(a) said acid group-containing monomers are selected from acrylic acid, methacrylic acid, 2-acrylamido-2-methyl propane sulfonic acid, and combinations thereof; and
(b) said cross-linking agent is selected from
(i) di- and polyvinyl compounds;
(ii) di- and polyesters of unsaturated mono- and polycarboxylic acids with polyols;
(iii) bisacrylamides;
(iv) carbamyl esters obtained by reacting polyisocyanates with hydroxyl-group containing monomers;
(v) di- and polyallyl ethers of polyols;
(vi) di- and polyallyl esters of polycarboxylic acids;
(vii) esters of unsaturated mono- and polycarboxylic acids with mono-allyl esters of polyols; and
(viii) di- and triallyl amines.

16. A process according to claim 15 wherein the aqueous reaction mixture comprises
(a) from about 8% to 24% by weight of the acid group-containing monomers;
(b) from about 0.01 mole percent to 3 mole percent of the cross-linking agent; and
(c) from about 0.001 mole percent to 0.5 mole percent of the free radical initiator; and
wherein the polymerization conditions to which said reaction mixture is subjected include a polymerization temperature of from about 5° C. to 40° C.

17. A process according to claim 16 wherein the free radical initiator comprises a peroxygen compound or comprises a redox initiator system formed by combining a peroxygen compound with a reducing agent.

18. A process according to claim 17 wherein the peroxygen compound initiator is selected from sodium, potassium, and ammonium persulfates, caprylyl peroxide, benzoyl peroxide, hydrogen peroxide, cumene hydroperoxides, t-butyl diperphthalate, t-butyl perbenzoate, sodium peracetate and sodium percarbonate, and wherein the redox initiator system comprises the combination of any of said peroxygen compound initiators with a reducing agent selected from sodium bisulfite, L-ascorbic acid and ferrous salts.

19. A process according to claim 18 wherein the initiator, or a component thereof, is incrementally added to the aqueous reaction mixture only in such amounts as are sufficient to promote complete polymerization of the acid group-containing monomers and cross-linking agents.

20. A process according to claim 13 which comprises the additional step of drying the polymer material produced in said aqueous reaction mixture.

21. A process according to claim 20 wherein said drying step is accomplished either by subjecting said polymer material to a temperature of from about 40° C. to 150° C. for a period of time sufficient to form a semi-solid mass of hydrogel-forming polymer material, by treating said polymer material with a dewatering solvent or by removing water from said polymer material via azeotropic distillation.

22. A process according to claim 13 wherein the aqueous reaction mixture is suspended in the form of droplets in a water-immiscible organic solvent, and wherein said droplets are subjected to polymerization conditions using inverse suspension or inverse emulsion polymerization procedures.

23. A process for preparing a substantially water-insoluble, slightly cross-linked, partially neutralized hydrogel-forming polymer material suitable for use in absorbent products, said process comprising
(a) preparing a reaction mixture consisting essentially of from about 8% to 24% by weight of polymerizable acrylic acid monomers in the free acid form, from about 0.01 mole percent to 3 mole percent, based on total moles of polymerizable monomers, of a cross-linking agent selected from N,N'-methylenebisacrylamide, trimethylol propane triacrylate and triallyl amine, and from about 0.001 mole percent to 0.5 mole percent, based on the total moles of acrylic acid plus cross-linking agent monomers, of a free radical initiator in an aqueous medium which is substantially free of graft polymerizable polymer moieties;
(b) subjecting said aqueous reaction mixture to polymerization conditions, including a temperature of from about 5° C. to 40° C., which are sufficient to produce therein a substantially water-insoluble, slightly cross-linked polyacrylic acid-based polymer material having, upon subsequent neutralization and drying, a gel volume, v, of from about 25 to 80 grams of synthetic urine per gram of hydrogel-forming polymer, a gel strength such that said hydrogel formed from said polymer material exhibits a shear modulus, s, of from about 2500 to 92,000 dynes/cm$^2$, an initial extractable polymer content, after one hour in synthetic urine, of no more than about 5% by weight of hydrogel-forming polymer, an equilibrium extractable polymer content, e, at equilibrium in synthetic urine, of no more than about 10% by weight of hydrogel-forming polymer, a relationship between gel volume, v, and equilibrium extractable polymer content, e, defined by the equation: $e \leq 0.23v - 3.0$, and a relationship between gel volume, v, and shear modulus, s, defined by the equation: $\log s \geq -2.494 \log v + 8.090$; and
(c) neutralizing at least a portion of the carboxyl groups of said polyacrylic acid-based polymer material formed in the aqueous reaction mixture with sodium cations to form a partially neutralized polymer material having a degree of neutralization of at least about 50%.

24. An absorbent structure suitable for use in disposable absorbent articles, said absorbent structure comprising:
(a) from about 50% to 98% by weight of said structure of hydrophilic fiber material; and
(b) from about 2% to 50% by weight of said structure of discrete particles of substantially water-insoluble, slightly cross-linked, partially neutralized, substantially dry, hydrogel-forming polymer material; wherein said polymer material has a degree of neutralization of at least about 25% and is substantially free of graft polymerizable polymer moieties; and further wherein said polymer material, upon neutralization to a degree of neutralization of at least 50%, has or would have a gel volume, v, of at least about 20 grams of synthetic urine per gram of hydrogel-forming polymer, a gel strength such that the hydrogel formed from said polymer material exhibits a shear modulus, s, of at least about 2000 dynes/cm$^2$, an initial extractable polymer content, after one hour in synthetic urine, of no more than about 7.5% by weight of hydrogel-forming polymer, and an equilibrium extractable polymer content, e, at equilibrium in synthetic urine, of no more than about 17% by weight of hydrogel-forming material.

25. An absorbent structure according to claim 24 wherein said hydrogel-forming polymer material
(a) has a degree of neutralization of at least about 50%;
(b) has a gel volume of from about 25 to 80 grams of synthetic urine per gram of hydrogel-forming polymer;
(c) forms a hydrogel material which exhibits a shear modulus of from about 2500 to 92,000 dynes/cm$^2$;
(d) has an initial extractable polymer content, after one hour in synthetic urine, of no more than about 5% by weight of hydrogel-forming polymer; and
(e) has an extractable polymer content, at equilibrium in synthetic urine, of no more than about 10% by weight of hydrogel-forming polymer.

26. An absorbent structure according to claim 24 wherein the hydrophilic fiber material comprises from about 65% to 90% by weight of said structure and wherein said polymer particles comprise from about 10% to 35% by weight of said structure.

27. An absorbent structure according to claim 24 which has a density of from about 0.06 to 0.3 grams/cm$^3$.

28. An absorbent structure according to claim 24 wherein said polymer material, prior to neutralization, comprises polymerized monomers selected from acrylic acid, methacrylic acid, 2-acrylamido-2-methyl propane sulfonic acid and combinations thereof, cross-linked with a cross-linking agent selected from (a) di- and polyesters of unsaturated mono- and polycarboxylic acids with polyols, (b) bisacrylamides and (c) di- and triallyl amines.

29. An absorbent structure according to claim 28 wherein said absorbent structure has a density of from about 0.09 to 0.18 g/cm$^3$, a basis weight of from about 0.02 to 0.12 g/cm$^2$ and wherein said absorbent structure comprises a mixture of wood pulp fibers and polymer particles having a particle size of from about 50 microns to 1 mm.

30. An absorbent structure according to claim 24 wherein, for the hydrogel-forming polymer particles, the relationship between gel volume, v, and equilibrium extractable polymer content, e, is defined by the equation: $e \leq 0.23v - 3.0$.

31. An absorbent structure according to claim 24 wherein, for the hydrogel-forming polymer particles, the relationship between gel volume, v, and equilibrium extractable polymer content, e, is defined by the equation: $e \leq 0.23v - 3.0$; and wherein the relationship between gel volume, v, and shear modulus, s, of the hydrogel formed from said particles is defined by the equation:

$$\log s \geq -2.494 \log v + 8.090.$$

32. An absorbent article comprising:
 (a) a liquid impervious backing sheet;
 (b) a liquid pervious, relatively hydrophobic topsheet; and
 (c) an absorbent core comprising an absorbent structure according to claim 24 positioned between said backing sheet and said topsheet.

33. A diaper article comprising:
 (a) a liquid impervious backing sheet;
 (b) a relatively hydrophobic, liquid pervious topsheet; and
 (c) an absorbent core positioned between said backing sheet and said topsheet, said absorbent core comprising an absorbent structure which consists essentially of
  (i) from about 65% to 90% by weight of said structure of hydrophilic fiber material; and
  (ii) from about 10% to 35% by weight of said structure of discrete particles of substantially water-insoluble, slightly cross-linked, partially neutralized, substantially dry hydrogel-forming polymer material comprising polymerized acrylic acid monomers, cross-linked with a cross-linking agent selected from N,N'-methylenebisacrylamide, trimethylol propane triacrylate and triallyl amine; wherein said polymer material has at least 50% of its acrylic acid groups neutralized with sodium cations and is substantially free of graft polymerized polymer moieties, and further wherein said hydrogel-forming polymer material has a gel volume, v, of at least about 20 grams of synthetic urine per gram of hydrogel-forming polymer, a gel strength such that the hydrogel formed from said polymer material exhibits a shear modulus, s, of at least about 2000 dynes/cm$^2$, an initial extractable polymer content, after one hour in synthetic urine, of no more than about 7.5% by weight of hydrogel-forming polymer, and an equilibrium extractable polymer content, e, after 16 hours in synthetic urine, of no more than about 17% by weight of hydrogel-forming polymer.

34. A diaper article according to claim 33 wherein the absorbent core comprises an hourglass-shaped absorbent structure formed from an air-laid mixture of hydrophilic fiber material and hydrogel-forming polymer particles.

35. A diaper article according to claim 33 wherein the polymer-containing absorbent structure comprises an insert positioned underneath an upper layer of the diaper core, which upper layer is hourglass-shaped and consists essentially of wood pulp fiber material and from 0% to about 8% by weight of particles of hydrogel-forming polymer material.

36. A diaper article according to claim 33 wherein, for said polymer particles, the relationship between gel volume, v, and equilibrium extractable polymer content, e, is defined by the equation: $e \leq 0.23v - 3.0$.

37. A diaper article according to claim 33 wherein, for said polymer particles, the relationship between gel volume, v, and equilibrium extractable polymer content, e, is defined by the equation: $e \leq 0.23v - 3.0$ and wherein the relationship between gel volume, v, and shear modulus, s, of the hydrogel formed from said particles is defined by the equation:

$$\log s \geq -2.494 \log v + 8.090.$$

* * * * *